United States Patent
Lin et al.

(10) Patent No.: US 10,709,334 B2
(45) Date of Patent: Jul. 14, 2020

(54) INTRAOPERATIVE GUIDANCE SYSTEM FOR TUMOR SURGERY

(71) Applicants: Wei-Chiang Lin, Coral Gables, FL (US); Yinchen Song, Lebanon, NH (US)

(72) Inventors: Wei-Chiang Lin, Coral Gables, FL (US); Yinchen Song, Lebanon, NH (US)

(73) Assignee: The Florida International University Board of Trustees, Miami, FL (US)

( * ) Notice: Subject to any disclaimer, the term of this patent is extended or adjusted under 35 U.S.C. 154(b) by 100 days.

(21) Appl. No.: 15/727,981

(22) Filed: Oct. 9, 2017

(65) Prior Publication Data

US 2018/0042485 A1    Feb. 15, 2018

Related U.S. Application Data

(63) Continuation of application No. 15/118,384, filed as application No. PCT/US2015/015444 on Feb. 11, 2015.
(Continued)

(51) Int. Cl.
    *A61B 5/00* (2006.01)
    *A61B 5/1455* (2006.01)
    (Continued)

(52) U.S. Cl.
    CPC ........ *A61B 5/0075* (2013.01); *A61B 5/14553* (2013.01); *A61B 34/20* (2016.02);
    (Continued)

(58) Field of Classification Search
    None
    See application file for complete search history.

(56) References Cited

U.S. PATENT DOCUMENTS

| | | | |
|---|---|---|---|
| 6,377,841 B1 * | 4/2002 | Lin | A61B 5/0059 356/303 |
| 2002/0058865 A1 | 5/2002 | Cheng et al. | |

(Continued)

OTHER PUBLICATIONS

Palmer et al., "Monte Carlo-based inverse model for calculating tissue optical properties: Part II: Applicationto breast cancer diagnosis", Applied Optics, vol. 45, No. 5, Feb. 10, 2006, pp. 1072-1078.*
(Continued)

*Primary Examiner* — Katherine L Fernandez
(74) *Attorney, Agent, or Firm* — Saliwanchik, Lloyd & Eisenschenk

(57) ABSTRACT

The current invention pertains to a system and methods of identifying a site in a tissue of a patient as neoplastic or normal. The system comprises a source of electromagnetic signals; an optical probe which delivers the electromagnetic signals to a working end of the probe; a spectrometer which acquires diffuse reflectance electromagnetic signals returned from the site probed by the optical probe. The spectrometer processes the diffuse reflectance signals to produce a diffuse reflectance spectra which is transmitted to a system controller programmed to analyze the diffuse reflectance spectra to calculate hemoglobin concentration, hemoglobin oxygenation, and/or diffuse reflectance intensity of signals having wavelength of about 700 nm. These parameters are used to identify the site as neoplastic or normal. The system of current invention can be used in identifying neoplastic sites in brain in an intraoperative manner, for example, during a pediatric brain surgery.

22 Claims, 6 Drawing Sheets

Related U.S. Application Data

(60) Provisional application No. 61/938,376, filed on Feb. 11, 2014.

(51) Int. Cl.
 *A61B 34/20* (2016.01)
 *A61B 90/13* (2016.01)

(52) U.S. Cl.
 CPC ...... *A61B 90/13* (2016.02); *A61B 2034/2055* (2016.02); *A61B 2576/026* (2013.01)

(56) References Cited

U.S. PATENT DOCUMENTS

| | | | | | |
|---|---|---|---|---|---|
| 2004/0044287 | A1* | 3/2004 | Lin | ...................... | A61B 5/0059 600/475 |
| 2006/0173359 | A1* | 8/2006 | Lin | ...................... | A61B 5/4244 600/478 |
| 2010/0198080 | A1* | 8/2010 | Liu | ...................... | A61B 5/0071 600/477 |
| 2011/0105865 | A1 | 5/2011 | Yu et al. | | |
| 2013/0012794 | A1* | 1/2013 | Zeng | .................. | A61B 1/00186 600/328 |
| 2013/0338739 | A1* | 12/2013 | Bornstein | ............ | A61N 5/0613 607/91 |

OTHER PUBLICATIONS

Bydlon, T.M. et al., "Performance metrics of an optical spectral imaging system for intra-operative assessment of breast tumor margins," *Optics Express*, 2010, pp. 8058-8076, vol. 18, No. 8.

Chen, P-C. et al., "Spectral-profile-based algorithm for hemoglobin oxygen saturation determination from diffuse reflectance spectra," *Biomedical Optics Express*, 2011, pp. 1082-1096, vol. 2, No. 5.

* cited by examiner

ID
INTRAOPERATIVE GUIDANCE SYSTEM FOR TUMOR SURGERY

CROSS REFERENCE TO RELATED APPLICATIONS

This application is a continuation of co-pending U.S. application Ser. No. 15/118,384, filed Aug. 11, 2016, which is the national stage of international application No. PCT/US2015/015444, filed Feb. 11, 2015, which claims the benefit of U.S. Provisional Application Ser. No. 61/938,376, filed Feb. 11, 2014, the disclosures of which are hereby incorporated by reference in their entireties, including any figures, tables, or drawings.

GOVERNMENT SUPPORT

The subject invention was made with government support under Grant No. R15CA173617-01A1 awarded by the National Institutes of Health. The government has certain rights in the invention.

BACKGROUND OF INVENTION

Brain tumors continue to be the leading cause of death among all forms of pediatric cancer. In a report issued by the United States Central Brain Tumor Registry, based upon data collected from 2004 to 2007 across 48 states, more than 4000 new pediatric cases of brain tumor were predicted for 2011.[1] The three most common pediatric brain tumors are astrocytoma (~50%), medulloblastoma (20%), and ependymoma (10%). Dysembryoplastic neuroepithelial tumors, although benign, are congenital tumors that are strongly associated with seizures and occur frequently in children. For each of these pathologic entities, gross total surgical resection, when feasible, is the optimal initial treatment option.[2,3] Strong correlations between the extent of tumor resection and clinical outcomes, such as 10 year progression-free survival, have been reported by different groups.[4-8]

Currently, frameless stereotaxy is used intraoperatively to guide tumor resection. Frameless stereotactic navigation systems enable neurosurgeons to relate the position of a tracking probe to structures present in pre-operative computed tomography (CT) or magnetic resonance imaging (MRI) studies.[9-10] However, CT/MRI studies may not delineate exact brain tumor margins, especially when infiltrating, due to their limited sensitivity. Previous investigations have demonstrated that tumor cells are often found in the brain outside of tumor margins defined by CT and MRI studies.[11] Furthermore, the accuracy of surgical navigation systems is often diminished during surgical procedures, due to shifts in brain structures.[11-12] While this issue may be overcome using intraoperative MRI (iMRI), this technology is very expensive to install and operate and its image acquisition time is long.

A popular alternative for intraoperative brain tumor detection is ultrasonography. While affordable and convenient, its reliability in detecting tumors is less than that of iMRI. Gerganov et al. compared ultrasonography with iMRI and pointed out that ultrasound could be used to detect more-confined, deeply-located remnants of low- or high-grade tumors with high accuracy, though its accuracy is limited when detecting superficial remnants. In addition, ultrasound is less likely to differentiate tumor from peritumoral edema, which is also hyperechoic.

Due to the limitations of these existing techniques, neurosurgeons typically rely on visual inspection and/or on-site pathology to guide tumor resection. Visual inspection, unfortunately, can be subjective and sometimes inconclusive; on-site pathology can be time-consuming and often inaccurate based upon frozen sections alone. Thus, significant residual tumor cells frequently are left behind after surgical resection.

Optical spectroscopy uses light absorption and scattering to quantify tissue biochemical composition and morphological characteristics. It has the advantage of providing non-destructive, automated tissue characterization in real-time, without removing tissue. To date, optical spectroscopy has been widely used to study pathological and physiological features at the tissue and cell levels in vivo and in vitro.

Among the spectroscopic techniques used in biomedicine, fluorescence spectroscopy has been of particular interest, because quantities of two intrinsic fluorophores, NAD(P)H and flavin proteins, are strongly associated with metabolic states of tissue. In addition, fluorescence spectroscopy can be used to study abnormal blood vessel proliferation and fibrosis in tissue, because Type-I collagen is another prominent biological fluorophore.

Diffuse reflectance spectroscopy is another optical spectroscopy technique commonly used in optical tissue characterization. It allows detection of tissue structure and biochemical composition by monitoring the optical properties (e.g., absorption and reduced scattering coefficients) of tissue.[13]

One common utility of diffuse reflectance spectroscopy is the detection of tissue hemodynamics, based on the fact that oxy- and deoxy-hemoglobin possess unique absorption features.[14] Understanding and assessing Hb oxygenation and concentration provides valuable insights into the condition of tissue. It is not surprising, then, that regional Hb oxygenation and Hb concentration are highly-sought information in tissue injury and disease diagnosis.[15-20]

Optical diagnostic technologies provide a potential complementary solution for intraoperative brain tumor demarcation, as demonstrated by several research groups. Optical technologies have also been used in conjunction with exogenesis tumor labels, such as ALA, for intraoperative guidance of brain tumor resection.[21-24] Clinical trials conducted with the ALA-based fluorescence brain tumor demarcation system demonstrate significant improvement in completeness of brain tumor removal in adult patients with high-grade brain tumors. However, the applicability of this guidance system to pediatric populations remains uncertain, as the safety of ALA in children has not yet been evaluated. Furthermore, the ALA-based guidance system is most efficient only for high-grade brain tumors, because ALA can efficiently cross the compromised blood brain barrier that exists in these tumors.[25] Whether the blood brain barrier also breaks down in pediatric brain tumors remains unknown.

To make optical diagnostic technology applicable within an in vivo or intraoperative environment, a contact probe often is employed to achieve remote sensing from in vivo tissue in the sterile operating field. The probe typically is held by the hand of an operator. One common problem with such a practice is motion artifacts in the acquired data. Unintentional hand movements or tremors alter the pressure of the probe against the target tissue. Ultimately, these movements are incorporated into the data as noise or artifacts.

A couple of earlier reports have suggested that probe pressure does not significantly affect the fluorescence intensity of the cervix.[26] A similar finding was noted in a study in which Raman spectroscopy was used to detect precancerous lesions within the gastrointestinal tract.[27-28] However, several other studies have shown that excessive probe contact pressure, resulting from hand movements, can lead to strong alterations in the hemodynamic and metabolic characteristics of local tissue.[29-32] This issue must be addressed in order to maximize the efficiency of an optical diagnostic technology for intraoperative surgical guidance.

BRIEF SUMMARY

The current invention provides a real-time system that is capable of intraoperatively detecting the margins of tumors, for example, brain tumors, with high sensitivity to aid surgeons in their objective to safely and completely resect tumors without removing normal tissue. The system of the current invention can be used to identify and remove tumors from any tissue, for example, brain.

For example, the current invention provides an optical guidance system that can differentiate brain tumors from normal brain at the resection front based upon distinct intrinsic morphological, biochemical, and physiological attributes of neoplastic cells compared to normal cells.

The current invention provides a system for identifying a site in the tissue of a patient as neoplastic or normal. In one embodiment, the system of the current invention comprises:
  a) a source of electromagnetic signals;
  b) an optical probe coupled with the source of electromagnetic signals, wherein the optical probe delivers the electromagnetic signals to a working end of the probe;
  c) a spectrometer which acquires diffuse reflectance electromagnetic signals returned from the tissue site probed by the working end of the probe and wherein the spectrometer processes the diffuse reflectance signals to produce diffuse reflectance spectra of the returned diffuse signals;
  d) a system controller having a processor coupled with the spectrometer, wherein the system controller is programmed to:
    i) analyze the diffuse reflectance spectra to calculate one or more of:
      a) absolute hemoglobin concentration ([Hb]),
      b) absolute hemoglobin oxygenation ($SatO_2$),
      c) diffuse reflectance intensity of signals having wavelength of about 700 nm (such as, for example, Rd(700)),
    and
    ii) analyze [Hb], $SatO_2$, and/or Rd(700) relative to those from normal reference tissue sites to identify the tissue site as neoplastic or normal. In one embodiment, the sites are from the same patient.

The invention can be used to positively impact the management of brain tumors, for example, pediatric brain tumors, because it provides new means by which neurosurgeons can objectively optimize the outcomes of brain tumor surgeries, thereby improving the prognoses of patients, and reducing the emotional and financial burdens endured by patients and their families. Moreover, the current invention can be used to enhance other studies for characterizing the spatial and temporal physiological characteristics of epileptic cortex in vivo and, hence, aid in epilepsy surgery, for example, pediatric epileptic surgery.

The surgical guidance system of the current invention can make a significant impact to brain tumor surgery because it provides speedy and objective assessment to the brain tissue in the operating room, which allows surgeons to make an informed decision about the extent of tumor resection.

This system can be designed for specific use in any type of brain tumor patients, for example, adult patients and pediatric patients. It may be used in other tumor resection procedures with a modified tissue differentiation algorithm.

The current invention can be used to identify a site in a tissue, for example, brain, of a patient as neoplastic or normal. The current invention also provides methods of using the system to intraoperatively identify a site as neoplastic or normal and surgically remove the site from the tissue of the patient, for example, brain, if the site is identified as neoplastic.

BRIEF DESCRIPTION OF DRAWINGS

FIG. 1A shows the distribution of tumor and normal tissue sites, in accordance with their corresponding $nSatO_2$, n[Hb], and nRd(700). The open circles represent normal cortex tissue and the solid circles represent brain tumor tissue. FIG. 1B shows the Receiver Operating Characteristics (ROCs) from the discrimination methods based on single parameters ($nSatO_2$, n[Hb], and nRd(700)) as well as all three parameters combined.

FIG. 3A shows the prototype of a hybrid imaging spectroscopy system with the new diffuse reflectance acquisition scheme embedded. The Hastings lenses are used to relay the image from the image plane of the camera lens (mimicking a surgical microscope) to the CCD sensor of the camera and the detection plane of the diffuse reflectance measurement port. The optical fiber attached to the diffuse reflectance measurement port enables us to selectively measure the diffuse reflectance signal from an arbitrary point within the field of view of the imaging system. According to Eq. (1) and Eq. (2) (see, Example 2), this measured signal can be converted to diffuse reflectance if it is normalized to the illumination power at the point of detection. Multiple fibers may be attached to the diffuse reflectance measurement port to enable simultaneous investigation of multiple points on the subject. FIG. 3B shows the system attached to the beam splitter of a surgical microscope, which will be used in brain tumor surgery.

FIG. 5A shows the original picture of the exposed cortical surface. FIG. 5B shows the processed image with all blood vessels, including arteries, arterioles, veins, and venules highlighted. Note specular reflection from the cortical surface results in certain noticeable artifacts in the processed image. Hence, blood vessel density analysis should not be performed in these regions. FIG. 5C shows the Representative vessel density characteristics determined by the pixel density histogram. The upper panel is from a 50×50 pixel area within the zone of resection, and the lower panel is from an area outside the zone of resection. The vessel identification algorithm used here highlights the edge of the vessels, and the intensities of the highlighted pixels vary in accordance with the edge definition of the vessels (i.e., the sharper the edge, the higher the intensity). Currently, we are exploring other methodologies to quantify blood vessel density within areas of interest, as well as to separate veins/venules from arteries/arterioles more objectively.

DETAILED DISCLOSURE

Figures 1A, 1B:
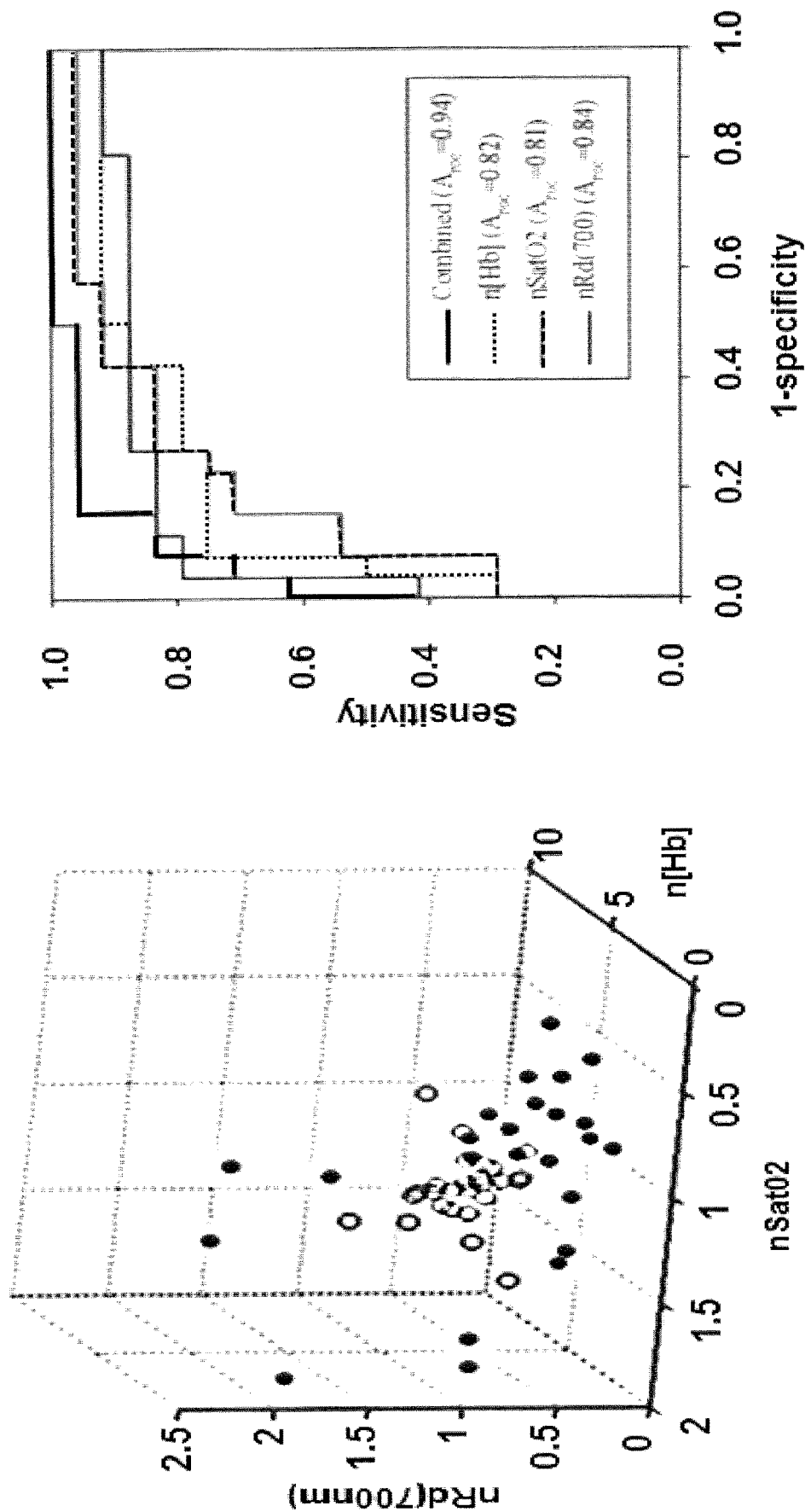
FIGS. 1A and 1B.

The current invention provides a system for identifying a site in the tissue of a patient as neoplastic or normal with high sensitivity and specificity. In general, embodiments of the hybrid spectroscopy and imaging system of the subject invention can include:

a) a source of electromagnetic signals;

b) an optical probe coupled with the source of electromagnetic signals, wherein the optical probe delivers the electromagnetic signals to a working end of the probe;

c) a spectrometer which acquires diffuse reflectance electromagnetic signals returned from the tissue site probed by the working end of the probe and wherein the spectrometer processes the diffuse reflectance signals to produce diffuse reflectance spectra of the returned diffuse signals;

d) a system controller having a processor coupled with the spectrometer, wherein the system controller is programmed to:

i) analyze the diffuse reflectance spectra to calculate one or more of:
   a) absolute hemoglobin concentration (e.g., [Hb]),
   b) absolute hemoglobin oxygenation (e.g., $SatO_2$),
   c) absolute diffuse reflectance intensity of signals having wavelength of about 700 nm (e.g., Rd(700)), and ii) analyze [Hb], $SatO_2$, and/or Rd(700) relative to those from normal reference tissue to identify the site as neoplastic or normal.

In a more specific embodiment, the hybrid spectroscopy and imaging system of the subject invention utilizes:

(1) an imaging device such as a surgical microscope;

(2) a source of electromagnetic signals that provides a broadband, large area of illumination;

(3) an image relay lens mounted at a secondary camera port of the imaging device in (1);

(4) an optical fiber adaptor placed at the imaging plane of the relay lens;

(5) one or more optical fibers with a small core diameter that are connected to the optical fiber adaptor to collect total diffuse reflectance electromagnetic signals;

(6) a spectrometer which acquires total diffuse reflectance electromagnetic signals collected by the optical fibers of (5) and produces total diffuse reflectance spectra of the returned diffuse signals;

(7) a system controller having a process coupled with the spectrometer, wherein the system controller is programmed to:

a. Analyze the total diffuse reflectance spectra to calculate one or more of:
   i. absolute hemoglobin oxygenation (e.g., SatO2),
   ii. absolute total diffuse reflectance intensity of signals having wavelength between 650 nm and 800 nm (e.g., Rd (700)),
   iii. relative ratio of absorption coefficient $\mu_a$ and reduced scattering coefficient $\mu_s$ between 450 nm and 650 nm (e.g., $\mu_a(\lambda)/\mu_s(\lambda)$), and b. Analyze SatO2, Rd(700), and/or $\mu_a(\lambda)/\mu_s(\lambda)$ relative to those from normal reference tissue sites of the same patient to identify the site as neoplastic or normal.

The system of the current invention can be utilized to identify a tissue site as neoplastic or normal in a variety of tissues, for example, brain, eyes, pineal gland, pituitary gland, thyroid gland, parathyroid glands, thorax, heart, lungs, esophagus, thymus gland, pleura, adrenal glands, appendix, gall bladder, urinary bladder, large intestine, small intestine, kidneys, liver, pancrease, spleen, stoma, prostate gland, testes, ovaries, or uterus.

In one embodiment of the invention, the system of the current invention is utilized to identify a site in the brain as neoplastic or normal.

The system of the current invention can also be configured to identify a site in the brain as epileptic or non-epileptic based on the $SatO_2$, Rd(700), and $\mu_a(\lambda)/\mu_s(\lambda)$.

In certain embodiments, of the hybrid spectroscopy imaging system of the subject invention, the system controller is programmed to analyze the total diffuse reflectance spectra to calculate SatO2 and Rd(700), and analyze SatO2 and Rd(700) to identify the tissue site as neoplastic or normal. In certain other embodiments, the system controller is programmed to analyze the diffuse reflectance spectra to calculate $SatO_2$ and $\mu_a(\lambda)/\mu_s(\lambda)$, and analyze $SatO_2$ and $\mu_a(\lambda)/\mu_s(\lambda)$ to identify the site as neoplastic or normal. In further embodiments, the system controller is programmed to analyze the diffuse reflectance spectra to calculate Rd(700) and $\mu_a(\lambda)/\mu_s(\lambda)$, and analyze Rd(700) and $\mu_a(\lambda)/\mu_s(\lambda)$ to identify the site as neoplastic or normal.

In one embodiment, the system controller is programmed to analyze the total diffuse reflectance spectra to calculate $SatO_2$, Rd(700), and $\mu_a(\lambda)/\mu_s(\lambda)$, and analyze $SatO_2$, Rd(700), and $\mu_a(\lambda)/\mu_s(\lambda)$ to identify the site as neoplastic or normal.

For the purposes of this invention, if a site in the tissue of a patient is identified as neoplastic, it indicates that the site contains cancerous cells; whereas, if a site in the tissue of a patient is identified as normal it indicates that the site is free from cancerous cells.

An electromagnetic signal refers to a wave of energy having a wavelength within the electromagnetic spectrum. An example of an electromagnetic wave is a light wave having a wavelength of 600 nm.

Electromagnetic signals refer to a group of waves having one or more frequencies within the electromagnetic spectrum. An example of electromagnetic signals is a beam of white light, which comprises a plurality of electromagnetic waves of different wavelengths.

The source of electromagnetic signals produces the electromagnetic signals comprising a plurality of electromagnetic waves of different wavelengths. For example, the electromagnetic signals comprising electromagnetic waves having wavelengths ranging from about 650 nm to about 800 nm refers to the electromagnetic signals comprising a plurality of waves, each wave having a wavelength within the range of about 650 nm to about 800 nm and the electromagnetic signals contain at least some waves of each wavelength falling within the range of about 650 to about 800 nm.

In certain embodiments of the invention, the electromagnetic signals comprise electromagnetic waves having wavelengths ranging from about 500 nm to about 900 nm, about 600 nm to about 850 nm, or about 650 nm to about 800 nm. In one embodiment of the invention, the electromagnetic signals comprise electromagnetic waves having wavelengths ranging from about 650 nm to about 800 nm.

The electromagnetic signals utilized by embodiments of the subject invention can have several sources, including, but not limited to:

the illumination light of an imaging device such as a surgical microscope;

an image relay lens mounted at a secondary camera port of an imaging device such as a surgical microscope;

an optical fiber adaptor placed at the imaging plane of the relay lens, where multiple fibers can be connected to the adaptor;

one or more optical fibers with a small core diameter that are connected to the optical fiber adaptor to collect total diffuse reflectance electromagnetic signals.

A spectrometer detects total diffuse reflectance electromagnetic signals collected by the optical fibers and produces total diffuse reflectance spectra of the returned diffuse signals.

An optical probe coupled with the source of electromagnetic signals transfers the electromagnetic waves to the working end of the probe. In one embodiment of the invention, the optical probe used to transfer the electromagnetic waves from the electromagnetic source to the working end of the optical probe is a fiber optic probe.

The working end of the optical probe is the end of the optical probe from which the electromagnetic signals emerge from the optical probe. This end of the optical probe delivers the electromagnetic signals.

For the purposes of this invention "probing a site with the optic probe" is intended to mean that the electromagnetic signals are delivered to the site by holding the working end of the optic probe in direct physical contact with the site.

A spectrometer acquires diffuse reflectance electromagnetic signals returned from the site probed by the working end of the optical probe. The spectrometer processes the diffuse reflectance signals to produce the diffuse reflectance spectra of the returned diffuse signals. In one embodiment of the invention, a set of 400 diffuse reflectance spectra is produced by the spectrometer.

In certain embodiments of the invention, the spectrometer acquires the diffuse reflectance electromagnetic signals returned from the site at a rate of about 5 Hz or higher, about 5 Hz to about 60 Hz, about 30 Hz to about 40 Hz, or about 60 Hz or higher. In one embodiment of the invention, the spectrometer acquires the diffuse reflectance electromagnetic signals returned from the site at about 33 Hz.

For the purposes of this invention, a system controller programmed to perform certain tasks indicates that the system controller is provided with a set of coded instructions that enables the system controller to perform a desired sequence of operations. In one embodiment of the invention, the system controller is a computer. The set of coded instructions that enables the system controller to perform a desired sequence of operations is called a software program or software.

The system controller having a processor coupled with the spectrometer is programmed to analyze the diffuse reflectance spectra to calculate (1) absolute hemoglobin oxygenation (e.g., SatO2), (2) absolute total diffuse reflectance intensity of signals having a wavelength between 650 nm and 800 nm (e.g., Rd(700)), (3) relative ratio of absorption coefficient $\mu_a$ and reduced scattering coefficient $\mu_s$ between 450 nm and 650 nm (e.g., $\mu_a(\lambda)/\mu_s(\lambda)$). The methods of calculation are known to those with ordinary skill in the art.

For example, methods of calculation can be found in published scientific articles.[34-35] Additional methods for calculating Rd(700) and $SatO_2$ using diffuse reflectance spectra are well known to a person of ordinary skill in the art.

In certain embodiments of the invention, the system controller is programmed to identify the site as neoplastic if:

$n\mu_a(\lambda)/\mu_s(\lambda) > 1 + x \times n\mu_a(\lambda)/\mu_s(\lambda)_{N\_std}$ or $n\mu_a(\lambda)/\mu_s(\lambda) < 1 - x \times \mu n_a(\lambda)/\mu_s(\lambda)_{N\_std}$, wherein x is an adjustable cutoff for $n\mu_a(\lambda)/\mu_s(\lambda)$ and $n\mu_a(\lambda)/\mu_s(\lambda)_{N\_std}$ is standard deviation of $n\mu_a(\lambda)/\mu_s(\lambda)$ from a plurality of known normal sites.

In certain other embodiments, the system controller is programmed to identify the site as neoplastic if:

$nSatO_2 > 1 + y \times SatO_{2N\_std}$ or $nSatO_2 < 1 - y \times SatO_{2N\_std}$, wherein y is an adjustable cutoff for $nSatO_2$ and $nSatO_{2N\_std}$ is standard deviation of $nSatO_2$ from the plurality of known normal sites.

In further embodiments, the system controller is programmed to identify the site as neoplastic if:

$nRd(700) > 1 + z \times Rd(700)_{N\_std}$ or $Rd(700) < 1 - z \times Rd(700)_{N\_std}$, wherein z is an adjustable cutoff and nRd(700) and $nRd(700)_{N\_std}$ is standard deviation for nRd(700) from the plurality of known normal sites.

In even further embodiments, the system controller is programmed to identify the site as neoplastic if:

a) any one of $nSatO_2$, and nRd(700), and $n\mu_a(\lambda)/\mu_s(\lambda)$ is $> 1 + u \times (stand\_deviation)$, or b) any one of $nSatO_2$, and nRd(700), and $n\mu_a(\lambda)/\mu_s(\lambda)$ is $< 1 - u \times (stand\_deviation)$, wherein u is an adjustable cutoff value for $nSatO_2$, or nRd(700), and $n\mu_a(\lambda)/\mu_s(\lambda)$ and (stand_deviation) is the standard deviation for the selected parameter from the plurality of known normal sites.

In additional embodiments, the system controller is programmed to identify the site as neoplastic if:

a) any two of $nSatO_2$, nRd(700), and $n\mu_a(\lambda)/\mu_s(\lambda)$ is $> 1 + v \times (stand\_deviation)$, or b) any two of $nSatO_2$, nRd(700), and $n\mu_a(\lambda)/\mu_s(\lambda)$ - is $< 1 - v \times (stand\_deviation)$, wherein v is an adjustable cutoff value for $nSatO_2$, nRd(700), and $n\mu_a(\lambda)/\mu_s(\lambda)$ and (stand_deviation) is the standard deviation for the selected parameters from the plurality of known normal sites.

In certain other embodiments, the system controller is programmed to identify the site as neoplastic if:

a) all of $nSatO_2$, nRd(700), and $n\mu_a(\lambda)/\mu_s(\lambda)$ - are $> 1 + w \times (stand\_deviation)$, or b) all of $nSatO_2$, nRd(700), and $n\mu_a(\lambda)/\mu_s(\lambda)$ - are $< 1 - w \times (stand\_deviation)$, wherein w is an adjustable cutoff value for $nSatO_2$, nRd(700), and $n\mu_a(\lambda)/\mu_s(\lambda)$ and (stand_deviation) is the standard deviation for the selected parameters from the plurality of known normal sites.

For the purposes of this invention, the term "adjustable cutoff value" for a particular parameter is a pre-determined value that is used to identify whether a site is neoplastic or normal. The adjustable cutoff value can be between about 0.5 to about 4.0, about 0.75 to about 3.0, about 1.0 to about 2.0, or about 1.25 to about 1.75. In one embodiment of the invention, the adjustable cut off value for a particular parameter is about 1. In another embodiment of the invention, the adjustable cut off value for a particular parameter is about 2.

The current invention also provides a method of using the system to identify a site in the tissue, for example, brain tissue, of a patient as neoplastic or normal. The method of using the system of the current invention comprises the steps of:

a) delivering the electromagnetic signals to the site and surrounding areas (i.e., large illumination area), b) acquiring total diffuse reflectance electromagnetic signals at the camera port of an imaging system, such as a surgical microscope, wherein the spectrometer detects total diffuse reflectance electromagnetic signals collected by the optical fibers and produces total diffuse reflectance spectra of the returned diffuse signals;

c) transmitting the total diffuse reflectance spectra from the spectrophotometer to the system controller having the processor coupled with the spectrometer, wherein the system controller is programmed to:

a) analyze the total diffuse reflectance spectra to calculate one or more of:
  i) absolute hemoglobin oxygenation (e.g., nSatO2),
  ii) absolute total diffuse reflectance intensity of signals having wavelengths between 650 nm and 800 nm (e.g., nRd(700)),
  iii) relative ratio of absorption coefficient $\mu_a$ and reduced scattering coefficient $\mu_s$ between 450 nm and 650 nm (e.g., $n\mu_a(\lambda)/\mu_s(\lambda)$)), and d) analyze nSatO2, nRd(700), and/or $n\mu_a(\lambda)/\mu_s(\lambda)$ relative to those from normal reference sites of the same patient to identify the site as neoplastic or normal.

In certain embodiments of the invention, the method is performed intraoperatively, e.g., the method is performed during the course of a surgery. In certain other embodiments of the invention, the method of identifying a site as neoplastic or normal further comprises removing the site from the brain of the patient if the site is identified as neoplastic.

In certain embodiments of the invention, the site is smaller than about 10 mm in diameter and about 5 mm in thickness. In certain other embodiments, the site is smaller than about 5 mm in diameter and about 2 mm in thickness. In further embodiments of the invention, the site is about 4 mm, about 3 mm, about 2 mm, or about 1 mm in diameter and about 5 mm, 4 mm, 3 mm, 2 mm, and 1 mm in thickness.

The method of the current invention can be performed on an adult patient or a pediatric patient, i.e. a child. In certain embodiments the child is less than 10, 9, 8, 7, 6, 5, 4, 3, 2, or 1 years of age.

The current invention also provides a procedure of determining the margins of a tumor in an organ. The procedure comprises identifying a plurality of sites in the organ as neoplastic or normal according to the methods and systems of the current invention, and providing the information about the plurality of sites to an apparatus which is programmed to represent the margins of the tumor in the organ in a graphical manner.

The organ can be selected from brain, eyes, pineal gland, pituitary gland, thyroid gland, parathyroid glands, thorax, heart, lungs, esophagus, thymus gland, pleura, adrenal glands, appendix, gall bladder, urinary bladder, large intestine, small intestine, kidneys, liver, pancrease, spleen, stoma, prostate gland, testes, ovaries, or uterus.

In one embodiment of the invention, the methods of the current invention are used to determine the margins of a brain tumor, for example, in an adult or a pediatric patient.

Example 1: Detecting Brain Tumors by Using Diffuse Reflectance Signals, Hemoglobin Oxygenation, and Hemoglobin Concentration Both in vitro and in vivo study results show that diffuse reflectance signals in the long wavelength region (e.g. between 650 nm and 800 nm) are efficient at differentiating a brain tumor from normal brain tissue.[33] This spectral feature reflects the structural characteristics of a tissue. The current invention demonstrates that adding regional hemodynamic characteristics (e.g. hemoglobin oxygenation (nSatO$_2$) and hemoglobin concentration (n[Hb]) further enhances the accuracy of differentiation.

Twelve pediatric patients, between one and 18-years old, were recruited to participate in a clinical study. Diffuse reflectance spectra were obtained from the in vivo brains of participants during craniotomy procedures for tumor resection, using a fiber optic based spectroscopy system.[44] During spectral data acquisition, the optical probe was held by the neurosurgeon and was in direct contact with the brain tissue. Optical measurements were taken from areas away from the resection zone (i.e., normal sites) and from areas within the resection zone (tumor sites). A set of 400 diffuse reflectance spectra Rd($\lambda$) was acquired from each investigation site at a rate of ~33 Hz. Following each spectral acquisition sequence, a baseline measurement Rd($\lambda$)$_{base}$ was conducted by turning off the electromagnetic signals source. At least three normal sites and three brain tumor sites were investigated during each patient study.

A specimen was collected from each investigated site within the resection zone for histopathological evaluation to identify the type of brain tumor. Biopsy samples were immediately fixed in a 10% formalin solution after resection. The specimens were then prepared for sectioning and hematoxylin and eosin staining. Processed slides were reviewed by a neuropathologist who was blinded to study results and other clinical information.

The baseline measurement Rd($\lambda$)$_{base}$ from each investigated site was first subtracted from the corresponding diffuse reflectance spectral set Rd($\lambda$) to remove unwanted ambient light influences. Then, instrumentally-induced spectral alterations were eliminated by dividing the spectra by a calibration spectrum Rd$_{cal}$($\lambda$). Note that the calibration spectrum was measured from a diffuse reflectance standard (FGS-20-02c, Avian Technologies, New Hampshire) using the same spectroscopic system. Mathematically speaking, the entire spectral calibration process can be described using the following equation: [Rd($\lambda$)−Rd($\lambda$)$_{base}$]/Rd$_{cal}$($\lambda$).

Three parameters extracted from each calibrated diffuse reflectance spectra were used to characterize the tissue site of investigation. These indicative parameters were n[Hb], nSatO$_2$, and nRd(700) (e.g., the diffuse reflectance intensity at 700 nm). The methods for estimating n[Hb] and nSatO$_2$ using diffuse reflectance spectra can be found in published, scientific articles, known to those with skill in the art. Since 400 continuous measurements were acquired from each investigated site, the mean value of each indicative parameter across the 400 measurements was used as a representative value. In order to reduce inevitable biological variations among all studied subjects, the indicative parameters from each patient were normalized to the average of the indicative parameters from the normal tissue sites of the same patient, which yielded n[Hb], nSatO$_2$, and nRd(700). In addition, the distributions of n[Hb], nSatO$_2$, and nRd (700) from all normal sites of the studied patients were assessed, and their standard deviations, denoted as n[Hb]$_{N\_std}$, nSatO2$_{N\_std}$ and nRd(700)$_{N\_std}$, respectively, were calculated.

The normalized indicative parameters described in the previous section were used to establish a classification system to differentiate brain tumor from normal brain (cortex). The classification criterion for each parameter is described as follows: (1) If n[Hb]>1+x×n[Hb]$_{N\_std}$ or n[Hb]<1−x×n[Hb]$_{N\_std}$, where x is an adjustable cutoff, the site was classified as neoplastic; otherwise, the site was classified as normal. Similarly, the tumor classification criteria for the two other parameters were designated (2) nSatO$_2$>1+x×nSatO$_{2N\_std}$ or nSatO$_2$<1−x×nSatO$_{2N\_std}$ and (3) nRd(700)>1+x×nRd(700)$_{Ns\_std}$ or nRd(700)<1−x×nRd(700)$_{N\_std}$, respectively.

The accuracies of these classification algorithms were quantified in terms of sensitivity and specificity, as well as through a receiver operating characteristic (ROC) curve. Moreover, a multi-variant classification criterion was established by combining the three classification criteria mentioned above. Using these combined criteria, a tissue site was classified as neoplastic if any one of the indicative parameters was outside the 1±x×(stand_deviation) boundaries. Here, the cutoff x values for all three parameters were identical. As with the single parameters, the performance of this multi-variant classification algorithm was characterized in terms of sensitivity, specificity, and ROC.

Comparing mean values, the average of nRd(700) from tumor measurements was lower than from normal brain. However, this trend was not observed in the n[Hb] and nSatO2 comparisons. Evaluation of the histograms of n[Hb] and $nSatO_2$ revealed a bi-modal distribution characteristic in the tumor measurements. When all three normalized indicative parameters from normal and tumor sites were plotted in a three-dimensional Cartesian coordinate system (FIG. 1A), the indicative parameters from normal cortex clearly formed a cluster centered with all parameters equal to one; conversely, parameters from tumors tended to scatter around the normal group cluster. FIG. 1B shows the ROCs and corresponding $A_{ROC}$ for all three individual classification criteria, as well as the multi-variant classification criterion. All three individual classification criteria performed satisfactorily, with $A_{ROC}$>0.8. The multi-variant criterion performed best, with $A_{ROC}$>0.9. The upper left point of the ROC of the multi-variant criterion is the result of the cutoff x=2 for all three parameters.

These thresholds also are plotted in FIG. 1A and form a cube in the figure. If the data points inside the cube are classified as normal and outside as tumor, this classifier yields a sensitivity of 95.8% and specificity of 84.6% within the patient pool studied.

Example 2: Development of a Hybrid Imaging and Spectroscopy System for Intraoperative Brain Tumor Demarcation While conducting the in vivo study described above, several difficulties associated with integrating a probe-based diagnostic system into a brain tumor resection procedure were noted. First, the ambient lights must be turned off to acquire accurate diffuse reflectance spectra; but this is difficult when a surgical microscope is used. Secondly, it may be difficult to maintain constant probe contact pressure during each spectral acquisition procedure, which usually lasts a few seconds. Finally, the probe may not be able to reach deep-seated tumors when the access channel is small. These shortcomings motivated the development of a new modality to conveniently detect artifact-free diffuse reflectance spectra from in vivo brain.

The diffuse reflectance characteristics of in vivo tissue may be acquired using a spectral imaging, known to those with skill in the art. With this approach, broad illumination and a wavelength selection mechanism (e.g., a liquid crystal tunable filter) are employed. Assuming that illumination is uniform and that the target is homogenous, the diffuse reflectance signal, Rd, from a single point (e.g., $r_d$=0) on the target surface, acquired by a spectral imaging system, can be described by the equation:

$$Rd(r_d=0)=c\int_{r=0}^{\infty}\int_{\theta=0}^{2\pi}f(r)rd\theta dr=c\int_{r=0}^{\infty}f(r)\times 2\pi rdr \qquad \text{Eq. (1)}$$

where c is a constant associated with the collection geometry of the imaging system; r is the distance between the source and the detection points; and f(r) is the diffuse reflectance signal from the same material illuminated by a pencil beam (e.g., point spread function).

Figure 2:
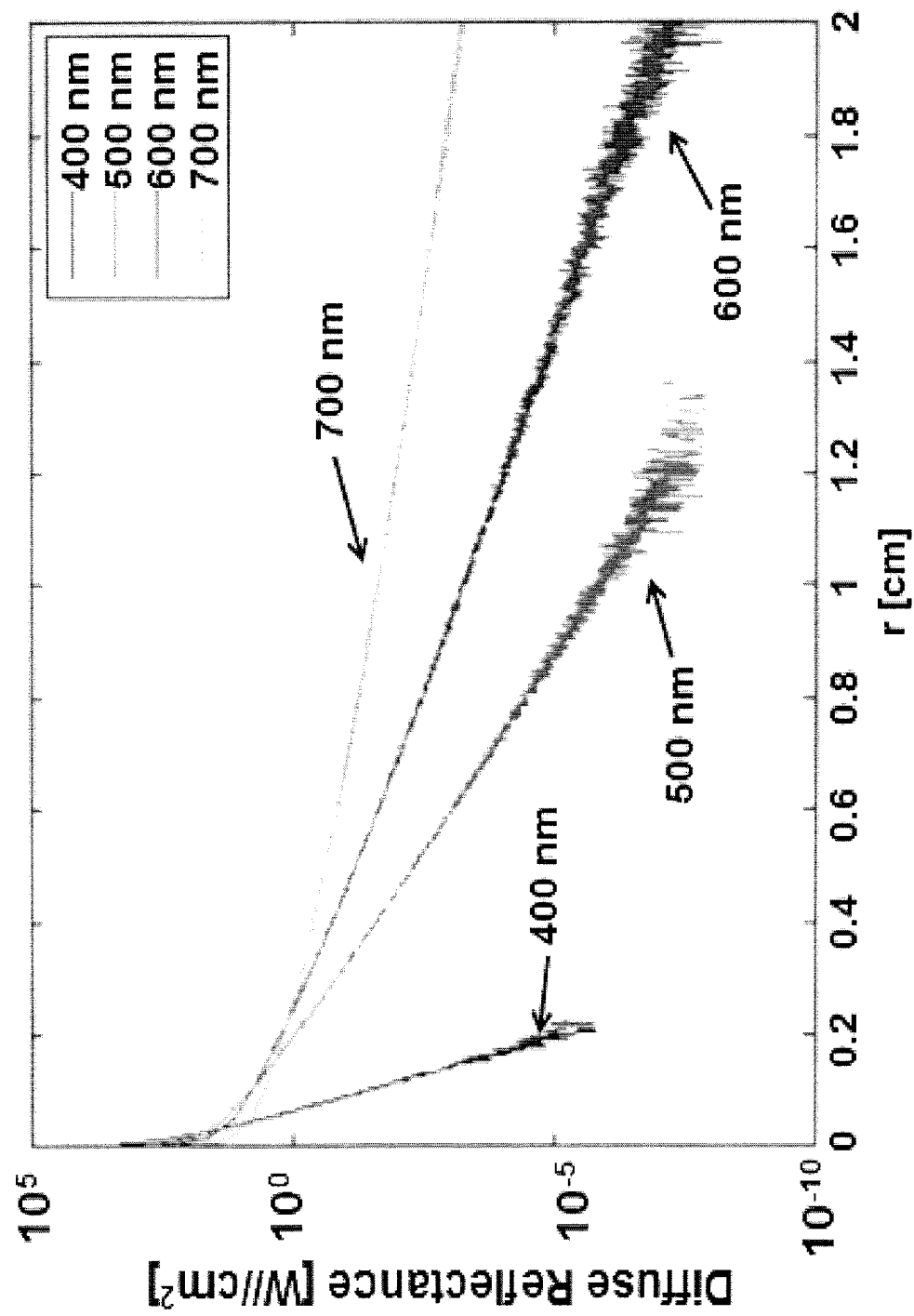
FIG. 2. Diffuse reflectance signal as a function of r, f(r), at four different wavelengths. Here individual f(r) was generated using a Monte Carlo (MC) simulation model for photon migration. Optical properties used in the simulation are those of human cortex at the four specified wavelengths; the illumination used is a pencil beam.

According to this equation, the contribution from the illumination point at r to the diffuse reflectance signal at the point of detection is identified by f(r), which is wider in the longer wavelength region (e.g., low reduced scattering coefficient $\mu'_s$ and absorption coefficient $\mu_a$), as shown in FIG. 2. In other words, the volume of investigation associated with the diffuse reflectance signals measured through the above-mentioned spectral imaging system increases significantly as the wavelength increases. This explains why diffuse reflectance spectra measured using a spectral imaging system differ greatly from those obtained using a conventional probe-based spectroscopic system, and how difficult it is to interpret them accurately.[64]

Assuming that an $I_p$ [W] pencil beam is used to illuminate a homogenous medium and that the resultant diffuse reflectance is f(r) [W/m²], the total reflectance $R_{TM}$ [%] can be calculated by $$R_{TM}=\int_{r=0}^{\infty}f(r)\times 2\pi rdr/I_p \qquad \text{Eq. (2)}$$

By comparing this formula with Eq. (1), the differences between the two equations are the collection factor in Eq. (1) and normalization to the illumination power of the pencil beam in Eq. (2). This similarity, in turn, suggests that diffuse reflectance signals measured from a surface point on an investigated subject using a spectral imaging system should be considered as total reflectance, instead of as a diffuse reflectance signal for an arbitrary source-detect separation. Based on this concept, a new detection scheme for diffuse reflectance spectroscopy was developed, as shown in FIG. 2. The advantage of this design is that it provides excellent spectral resolution in the measured diffuse reflectance spectra, as well as the feasibility of continuous spectral acquisition at a rate of 5 Hz or greater.

Figure 4:
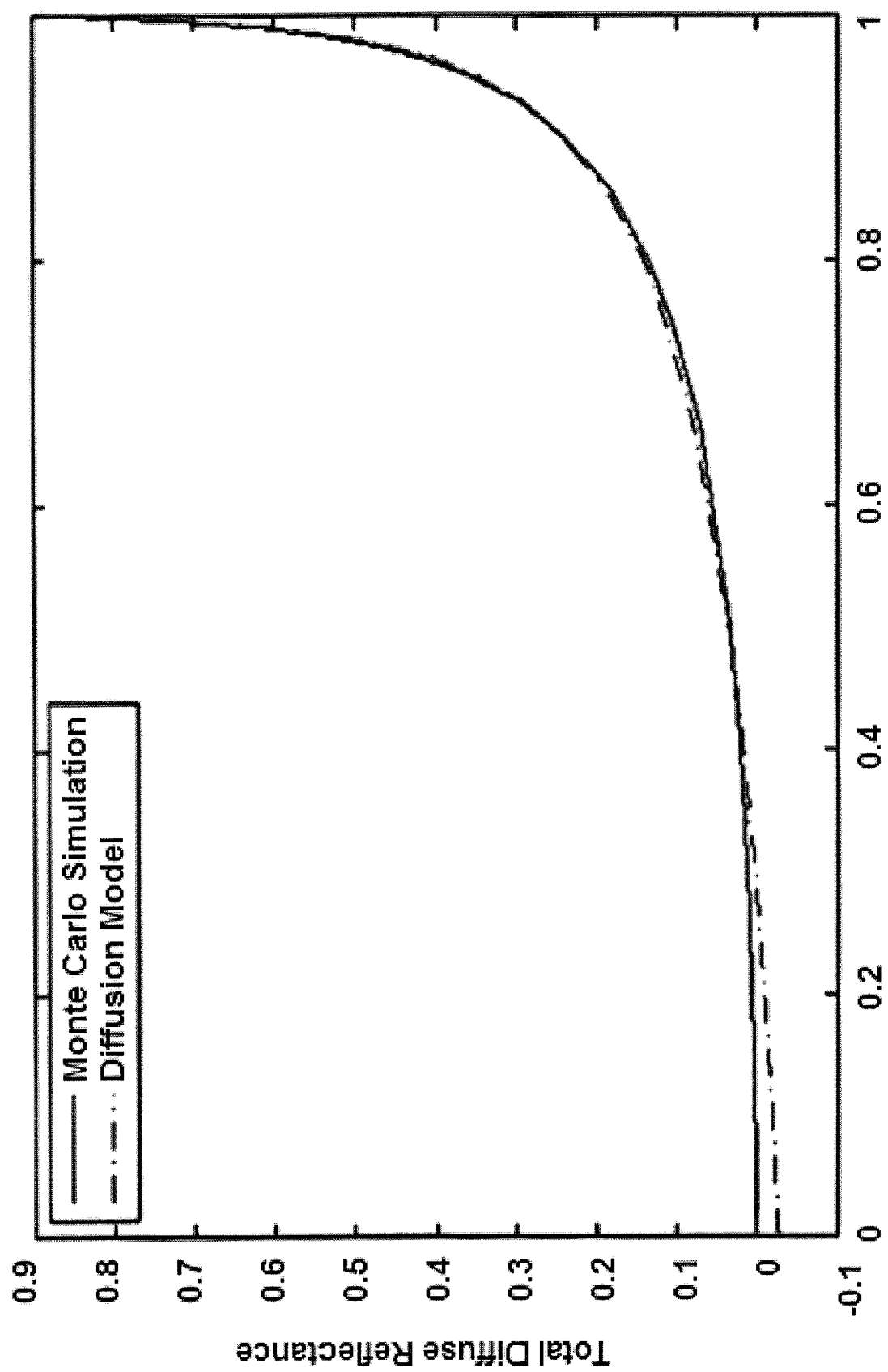
FIG. 4. Total diffuse reflectance $R_{T4}$ as a function of reduced albedo. The solid line is calculated using a MC simulation model for photon migration, the dash-line using the analytical model by Farrell et al.[36]

To convert total or diffuse reflectance signals to physiological parameters (e.g., hemodynamic and structural characteristics), a model for photon migration is required. Among all the possible options, we found that both the analytical total reflectance $R_{TA}$ model proposed by Farrell et al.[36] and the look-up table model based on a Monte Carlo simulation model for photon migration meet the requirements. It should be noted that both models indicate that $R_{TA}$ is a function of reduced albedo $a'=\mu'_s/(\mu'_s+\mu_a)$, as shown in FIG. 4. In a prior study conducted by our research group, we found that it is also possible to retrieve $nSatO_2$ information through the profile of a calibrated diffuse reflectance spectrum.[60, 61] We have modified the algorithm to make it applicable to total reflectance spectra.

In summary, this Example provides a new measurement scheme that can yield artifact-free total reflectance spectra $R_{TA}(\lambda)$, which can be easily integrated into the surgical environment.

Example 3: Validating the Efficiency of Diffuse Reflectance Spectroscopy in Guiding Brain Tumor Resection This Example shows that diffuse reflectance spectroscopy is effective in detecting pediatric brain tumors intraoperatively. To achieve this goal, the new diffuse reflectance measurement scheme, described in the Examples 1 and 2, is incorporated into a surgical microscope. The hybrid system is used to acquire artifact-free diffuse reflectance spectra from in vivo brain during brain tumor surgery, and the measured spectra are applied to the discrimination algorithm. The diagnostic results yielded by the discrimination algorithm are compared with the histological records, and the accuracy of the new intraoperative diagnostic system is identified. Details of this study are provided below.

Reflectance Standard Development

As indicated by Eq. (1) and Eq. (2), calculating total reflectance $R_{TM}$ using Rd requires prior knowledge about the power of the electromagnetic signals at the site of investigation, $I_0$. Quantitatively, $R_{TM}=Rd/(c \times I_0)$. The strategy we propose to quantify $I_0$ involves a disposable diffuse reflectance standard with known reflectivity (RF). To meet the needs of the in vivo human studies, the standard should possess the following properties. First of all, the material of the standard should be highly biocompatible and able to withstand the sterilization procedure (e.g., gas sterilization) used in the hospitals. Secondly, the angular dependence of Rd of the standard should be comparable to that of biological tissues. This will ensure that the collection geometry factor c in Eq. (1) does not introduce unwanted alterations to $R_{TM}$. Thirdly, the standard should have stable optical properties and be usable in a wet environment. In order to satisfy all the above criteria, we will test various materials that are used in the surgical field. The reflectivity (RF) of the evaluated material and the angular dependence of its Rd will be quantified, before and after treatments (e.g., wetting and sterilization), using a spectrophotometer and an optical goniometer. The material that processes the same angular dependence of Rd of biological tissue is used to fabricate disk-shape diffuse reflectance standards that are 5 mm in diameter and 2 mm thick. During an in vivo tissue investigation, one reference standard is placed on top of the investigated site, from which a reference diffuse reflectance spectrum ($Rd_{ref}$) is measured. Then, illumination power at the site of investigation can be estimated by $c \times I_0 = Rd_{ref}/RF$. Once the reference standard is removed, another diffuse reflectance spectrum is acquired from the target biological tissue ($Rd_{sample}$) Total reflectance from this investigated site is then calculated by $R_{TM}=(Rd_{sample} \times RF)/Rd_{ref}$. During this entire spectral acquisition procedure, the hybrid imaging system is not moved, so as to maintain constant collection geometry (i.e., c in Eq. (1)).

Spectral Interpretation Software Development

Figure 3B:
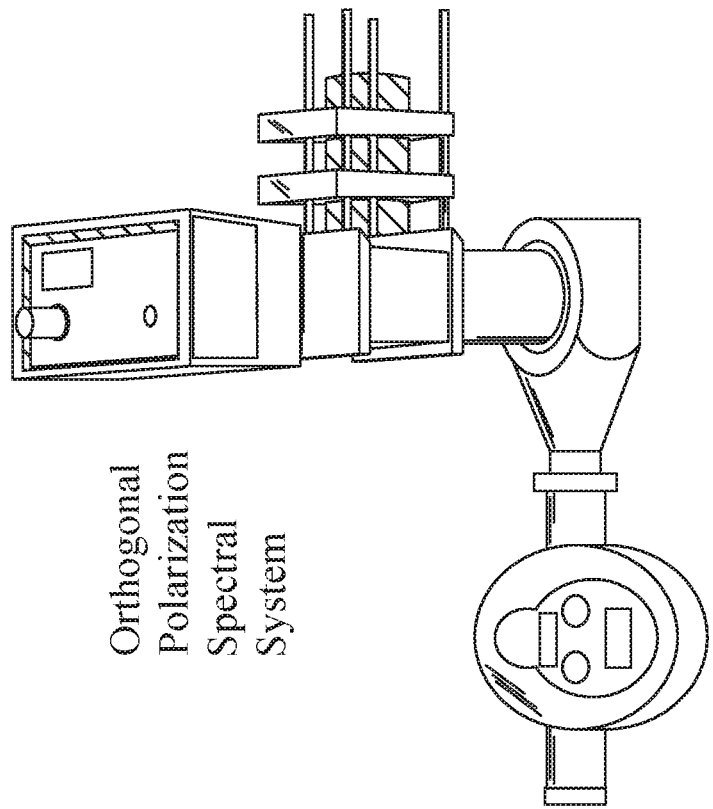
FIGS. 3A and 3B.
Figure 3A:
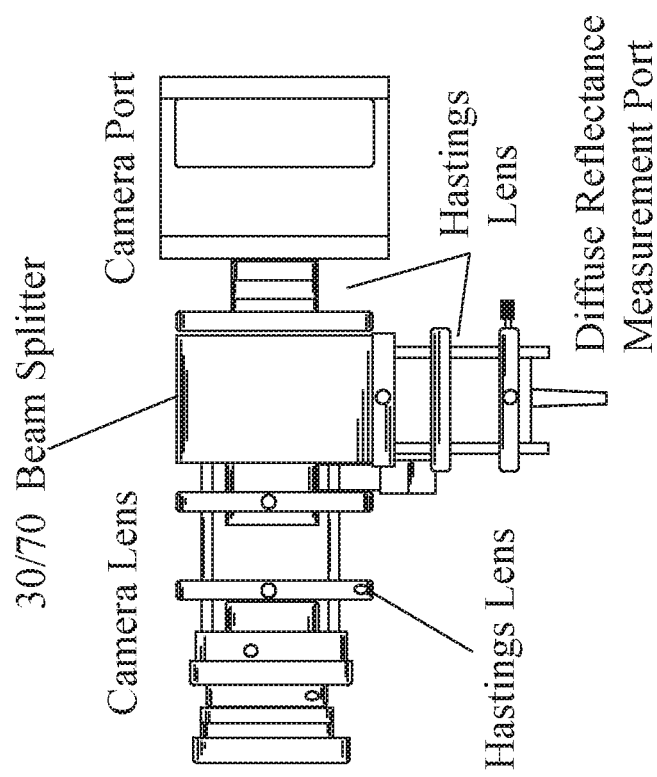

A software program processes and interprets $R_{TM}(\lambda)$. Briefly, $R_{TM}(\lambda)$ from each investigated site is used in conjunction with a spectral interpretation algorithm derived from published articles[60, 61] or otherwise known to a person of ordinary skill in the art to identify the absolute level of $SatO_2$. In addition, $R_{TM}(\lambda)$ is converted to $a'(\lambda)$ using the reference table shown in FIG. 4. This conversion can be limited to the spectral range of 400 to 600 nm, if the volume of investigation of the system is intended to be limited, e.g., <5 mm diameter. The mean and standard deviation of $nSatO_2$ and $a'(\lambda)$ from all normal tissue sites is calculated and then used to create the threshold in the tissue differentiation algorithm shown in Section 3.1 and FIG. 3A.

Evaluation of the Hybrid Imaging Spectroscopy System

The main purpose of this evaluation study is to quantify the measurement accuracy of the new diffuse reflectance measurement scheme, as well as the hybrid imaging system, for a wide range of optical properties as well as collection geometry (e.g., measurement distance and observation angle). The evaluation study is performed using tissue phantoms with known optical properties.[60] These phantoms consist of a mixture of whole blood (absorbers) and scatterers in a saline solution. The blood samples are heparinized after their acquisition from healthy human subjects. The scatterers added to the solution are 0.1, 0.5, 1.0, and 5.0 vim diameter microspheres (Polysciences Inc., Warrington Pa.). From the phantoms, total reflectance spectra ($R_{TM}$) is acquired using the hybrid system. The absorption and scattering properties derived from $R_{TM}$ are compared with those of the corresponding phantoms, and estimation errors quantified using statistical tools.

In Vivo Validation Study

We will verify the accuracy of the system developed for intraoperative brain tumor detection in an in vivo study. Here, histology is used as the gold standard for comparison. In addition, the accuracy of the system is compared with that of the intraoperative ultrasound and frameless stereotactic navigation systems (Brainlab Inc., Westchester, Ill.).

Total reflectance spectra are measured from brain tumors and normal brain in pediatric patients in vivo, using the hybrid imaging spectroscopy system developed in Example 2.

The study protocol described below is followed. For each patient studied, the optical investigation is performed prior to, during, and after brain tumor removal. To establish the ranges of optical/physiological parameters of normal brain tissue, five or more independent total reflectance spectra $R_{TM}(\lambda)$ are acquired from normal brain tissue (e.g., at least 2 cm away from the resection margin) prior to initiation of tumor resection. During the process of tumor removal, $R_{TM}(\lambda)$ are acquired from both the tumor core and tumor margins. Additional $R_{TM}(\lambda)$ are acquired when the surgeon approaches the resection margin to identify the sensitivity of the proposed optical system in detecting tumor margins. Prior to spectral acquisition, each investigated site will be rinsed gently with saline to remove surface blood and other debris.

With the detection point (e.g., the center point of the field of view of the surgical microscope) placed at the site of investigation, total reflectance spectra $R_{TM, Tissue}(\lambda)$ is acquired continuously for at least 3 seconds to verify the reproducibility of the spectral signals. Upon completing the spectral measurements at the investigated site, the reflection standard is placed on the site of investigation, and another set of total reflectance spectra $R_{TM, Ref}(\lambda)$ are acquired for reference purposes. It should be noted that the surface of the standard should be parallel to that of the investigated site, and that the surgical microscope should not be moved during the spectral acquisition procedure. Each investigated site is marked and its tissue characteristics identified on the appropriate pre-operative magnetic resonance (MR) images, as well as on intraoperative ultrasound images, using frameless stereotaxy. Each site is also categorized by the surgeon, by means of visual inspection, either as normal, tumor margin, or tumor center. Biopsies are taken from each investigated site, except when the investigated site is situated outside the resection margins. All biopsies are preserved in 10% formalin, and then processed and read by a neuropathologist. During histological evaluation, each biopsy sample is identified as either tumor or normal tissue, and the volume fraction of tumor (e.g., 100%, >75%, >50%, >25%, 0%) identified.

Data Analysis

Acquired spectra are processed using the procedure proposed in Example 2 to obtain the two indicative parameters representing the tissue characteristics: $nSatO_2$ and $a'(\lambda)$. Subsequently, these parameters are used in conjunction with the discrimination method described above to identify the characteristics of the investigated tissue. These classification results will be compared with their corresponding histological records. In this comparison, we will use sensitivity, specificity, and receiver operating characteristics (ROC)

analysis to quantify the accuracy of the current discrimination algorithm. Furthermore, the level of alterations in the indicative parameters are quantitatively compared with the tumor volume fraction identified by histology via correlation analysis, which should yield insights into the sensitivity as well as the detection limit of the total reflectance spectroscopy system proposed in this Aim. Finally, the accuracy of the optical guidance system is compared with those based on the intraoperative ultrasound, the frameless stereotactic navigation systems (MRI), and surgeons' visual inspection.

In this comparison, the histological identities of the investigated sites are used as the gold standard, against which the accuracy of the four modalities in detecting tumor margins is calculated.

Example 4: Identifying the Microscopic Flow and Vascular Architectural Characteristics of Brain Tumors Thereby Distinguishing them from Normal Brain The primary objective of this Example is incorporating the flow and vascular architectural characteristics of tumors to enhance brain tumor demarcation. Flow and vascular architectural characteristics can enhance the efficiency of intraoperative brain tumor demarcation.[37-40]

System Upgrade

The methodology for measuring the microcirculation characteristics employed in this Example will be orthogonal polarization spectral imaging.[41-42] To implement this methodology into the spectroscopy surgical microscope system mentioned in Example 3, the following modifications are done.

First, microscope illumination is polarized using a linear polarizer, which prevents any interference from specular reflection in the recorded images. Second, a camera system is attached to the beam splitter of the surgical microscope to which the point detection system is attached (FIG. 2). The camera system is designed in the way that it provides an additional 2× magnification. The camera used is a high-speed and high-resolution DSLR camera with video capture capability. The video frame rate should exceed 60 frames per second. A linear polarizer is mounted at the entrance of the camera system to eliminate specular reflection from the brain surface. In addition, an optical filter is used to select the band of diffuse reflection. For the purpose of studying the microscopic flow and vasculature characteristics of in vivo brain, diffuse reflectance images at 540 nm and 560 nm are recorded. The selection of these two wavelengths is based on the absorption characteristics of oxy- and deoxy hemoglobin. The system, once set up, is calibrated using layered tissue phantoms to identify its probing depth as a function of optical properties and to ascertain its functionality.

Quantification of Microvascular Flow Characteristics

A software program analyzes the video frames recorded using the imaging system to identify the flow characteristics of the microcirculation (arterioles and venules). Shifts in intravascular optical patterns over a defined time interval are used to calculate velocity by spatial correlation, a method developed for orthogonal polarization spectral imaging as well as intravital microscopy.[43-44] The overall data process time for this analysis is limited to 10 seconds or less, so the surgeons can receive the diagnostic feedback immediately in the operating room and use it to make surgical decision.

Quantification of Microvascular Architectural Characteristics

Figure 5B:
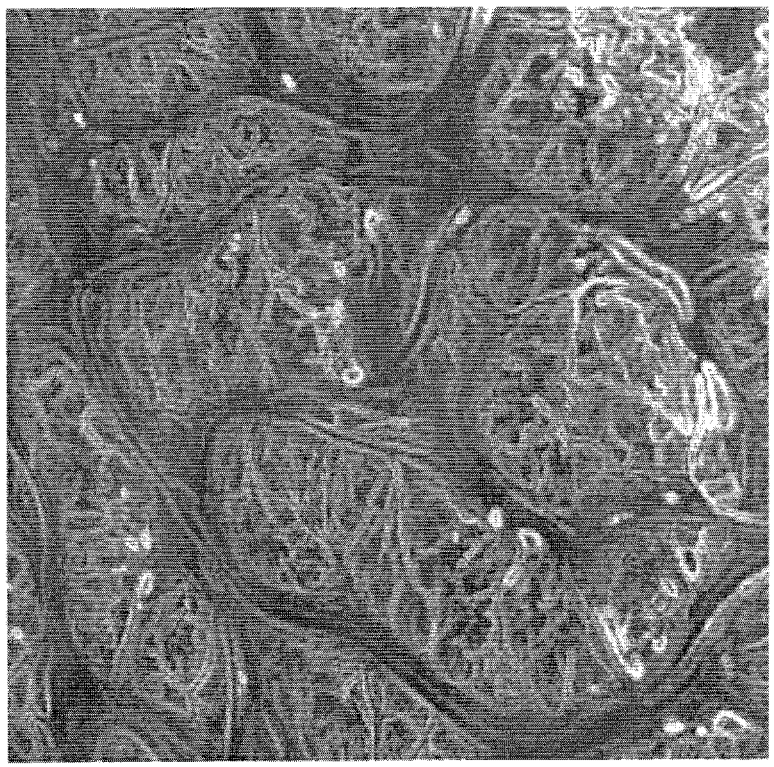
FIGS. 5A, 5B, and 5C. Cortical vasculature analysis using static photos.
Figure 5A:
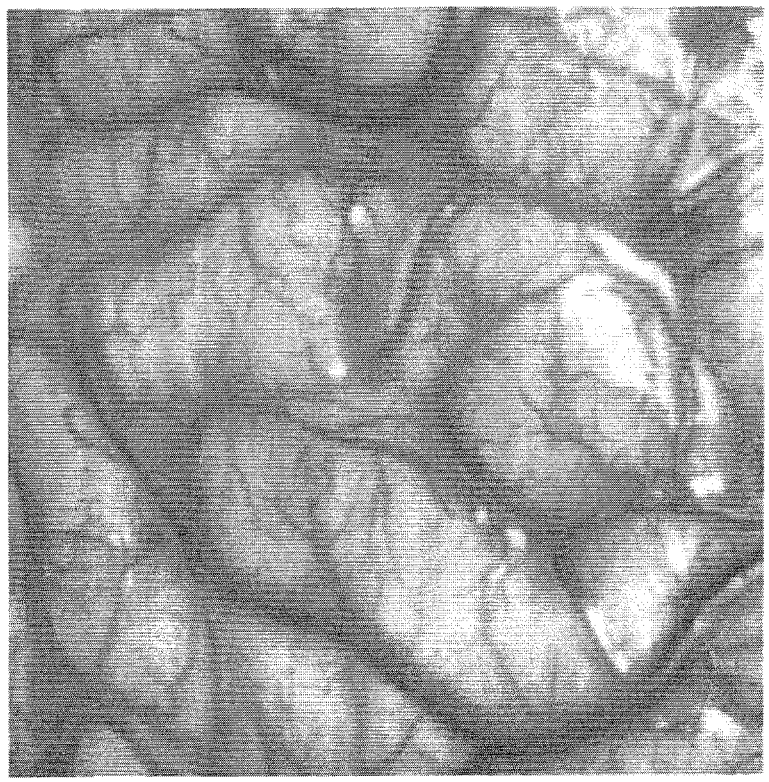
Figure 5C:
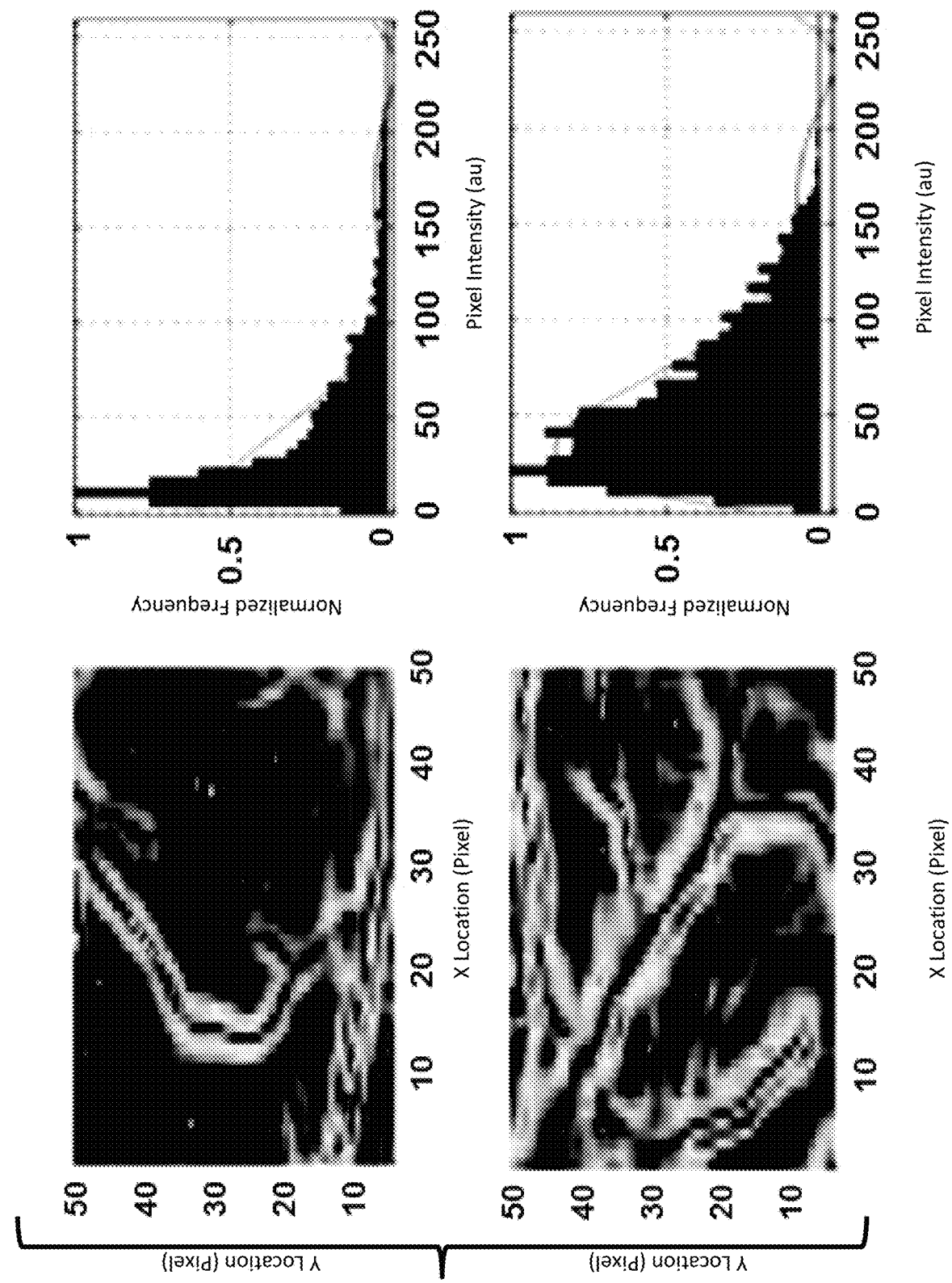

Images at the resection front are taken at 540 and 560 nm and then used to identify the characteristics of microvascular architecture. An imaging process technique called edge detection is applied to the image to highlight the blood vessels (arteries/arterioles and veins/venules). Using the ratio of these two images, the relative $SatO_2$ and, hence, separate arteries/arterioles from veins/venules are identified. To create quantitative indices for these regional microvascular architectural characteristics, the histogram of pixel intensity within a fixed window of the processed image can be used (see FIGS. 5A, 5B, and 5C) to represent vessel density within the area of interest. In addition, vessel length per area, the number of vessel segments per area, and mean vessel diameter to quantify the architectural features of the vasculature can be utilized. An image processing program can automate these measurements. The overall data process time for this analysis is limited to 5 seconds or less, so the surgeons can receive the diagnostic feedback immediately in the operating room and use it to make surgical decision.

In Vivo Validation Study

The usefulness of microscopic flow and microvascular architectural characteristics for intraoperative brain tumor/brain tumor margin detection in vivo is established. Here, histology is used as the gold standard. The study protocol and procedure are the same as that described in Reflectance Standard Development in Example 3. Video recording from the brain surface is performed while the diffuse reflectance spectra are acquired. The recording duration is 10 seconds for each site.

Data Analysis

The recorded video is processed using the two programs developed to quantify microvascular flow and microvascular architectural characteristics. This leads to the following parameters for each investigated site: blood flow velocity in arterioles and venules; blood flow kinetics (stop flow, spurt flow, and continuous flow); mean vessel diameter; total length of the vessels; and blood vessel density within the site of investigation. These parameters are analyzed collectively with the regional $SatO_2$ and $a'(\lambda)$, derived from $R_{TM}(\lambda)$. First of all, the normal ranges of these parameters are calculated using video recordings from normal cortex. In addition, the distribution characteristics (e.g., normal distribution) of these parameters from normal cortex are evaluated. Secondly, the ranges of these parameters from brain tumors and their margins are calculated and compared against those derived from normal cortex using non-parametric or parametric statistical comparison methods, as indicated. Parameters that demonstrate significant differences between normal cortex and tumor/tumor margins are used to reconstruct the discrimination algorithm mentioned in Example 1.

The efficiency of the new discrimination algorithm, in terms of intraoperative brain tumor detection, is evaluated via ROC analysis and compared against that of the original algorithm. Furthermore, the level of alterations in the indicative parameters are quantitatively compared with the tumor volume fraction identified by histology via correlation analysis, which yields insights into the sensitivity as well as the detection limit of the imaging modalities proposed in this Example.

All patents, patent applications, provisional applications, and publications referred to or cited herein, including those listed in the "References" section, are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

REFERENCES

1. *Statistical Report: Primary Brain and Central Nervous System Tumors Diagnosed in the United States in 2004-2007*. 2011; Available from: http://www.cbtrus.org/2007-2008/2007-20081.html.
2. Rutka, J. T. and J. S. Kuo, *Pediatric surgical neuro-oncology: current best care practices and strategies*. J Neurooncol, 2004. 69(1-3): p. 139-50.
3. Karajannis, M., J. C. Allen, and E. W. Newcomb, *Treatment of pediatric brain tumors*. J Cell Physiol, 2008. 217(3): p. 584-9.
4. Fernandez, C., et al., *Pilocytic astrocytomas in children: prognostic factors—a retrospective study of 80 cases*. Neurosurgery, 2003. 53(3): p. 544-53; discussion 554-5.
5. Pollack, I. F., et al., *Low-grade gliomas of the cerebral hemispheres in children: an analysis of 71 cases*. J Neurosurg, 1995. 82(4): p. 536-47.
6. Hirsch, J. F., et al., *Benign astrocytic and oligodendrocytic tumors of the cerebral hemispheres in children*. J Neurosurg, 1989. 70(4): p. 568-72.
7. Laws, E. R., Jr., et al., *Neurosurgical management of low-grade astrocytoma of the cerebral hemispheres*. J Neurosurg, 1984. 61(4): p. 665-73.
8. Mercuri, S., A. Russo, and L. Palma, *Hemispheric supratentorial astrocytomas in children. Long-term results in 29 cases*. J Neurosurg, 1981. 55(2): p. 170-3.
9. Maciunas, R. J., *Approaches to Frame-Based and Frameless Stereotaxis*. Minimally Invasive Therapy of the Brain, ed. A. D. Salles and R. Lufkin1997, New York: Thieme Medical Publishers, Inc.
10. Maciunas, R. J., *Pitfalls*, in *Image-guided neurosurgery: clinical applications of surgical navigation*, G. H. Barnett, D. W. Roberts, and R. J. Maciunas, Editors. 1998, Quality Medical Publishing, Inc.: St. Louis, Mo. p. 43-60.
11. Dorward, N., et al., *Postimaging brain distortion: magnitude, correlates, and impact on neuronavigation*. J Neurosurg, 1998. 88(4): p. 656-662.
12. Hill, D., et al., *Measurement of intraoperative brain surface deformation under a craniotomy*. Neurosurgery, 1998. 43(3): p. 514-526.
13. Cheong, W.-F., *Summary of optical properties*, in *Optical-thermal response of laser-irradiated tissue*, A. Welch and M. v. Gemert, Editors. 1995, Plenum Press: New York. p. 233-301.
14. Prahl, S. *Optical absorption of hemoglobin*. [Internet] 1999; Available from: http://omlc.ogi.edu/spectra/hemoglobin/index.html.
15. Siegemund, M., J. van Bommel, and C. Ince, *Assessment of regional tissue oxygenation*. Intensive Care Med, 1999. 25(10): p. 1044-60.
16. Benaron, D. A., et al., *Continuous, noninvasive, and localized microvascular tissue oximetry using visible light spectroscopy*. Anesthesiology, 2004. 100(6): p. 1469-75.
17. Verdant, C. and D. De Backer, *How monitoring of the microcirculation may help us at the bedside*. Curr Opin Crit Care, 2005. 11(3): p. 240-4.
18. Knotzer, H. and W. R. Hasibeder, *Microcirculatory function monitoring at the bedside—a view from the intensive care*. Physiol Meas, 2007. 28(9): p. R65-86.
19. Mallia, R., et al., *Oxygenated hemoglobin diffuse reflectance ratio for in vivo detection of oral pre-cancer*. J Biomed Opt, 2008. 13(4): p. 041306.
20. Wang, H. W., et al., *Diffuse reflectance spectroscopy detects increased hemoglobin concentration and decreased oxygenation during colon carcinogenesis from normal to malignant tumors*. Opt Express, 2009. 17(4): p. 2805-17.
21. Floeth, F. W., et al., *Comparison of (18)F-FET PET and 5-ALA fluorescence in cerebral gliomas*. Eur J Nucl Med Mol Imaging, 2011. 38(4): p. 731-41.
22. Pichlmeier, U., et al., *Resection and survival in glioblastoma multiforme: an RTOG recursive partitioning analysis of ALA study patients*. Neuro Oncol, 2008. 10(6): p. 1025-34.
23. Valdes, P. A., et al., *Quantitative fluorescence in intracranial tumor: implications for ALA-induced PpIX as an intraoperative biomarker*. J Neurosurg, 2011. 115(1): p. 11-7.
24. Veiseh, M., et al., *Tumor paint: a chlorotoxin:Cy5.5 bioconjugate for intraoperative visualization of cancer foci*. Cancer Res, 2007. 67(14): p. 6882-8.
25. Ennis, S. R., et al., *Transport of 5-aminolevulinic acid between blood and brain*. Brain Res, 2003. 959(2): p. 226-34.
26. Nath, A., et al., *Effect of probe pressure on cervical fluorescence spectroscopy measurements*. J Biomed Opt, 2004. 9(3): p. 523-33.
27. Shim, M. G., et al., *In vivo near-infrared Raman spectroscopy: demonstration of feasibility during clinical gastrointestinal endoscopy*. Photochem Photobiol, 2000. 72(1): p. 146-50.
28. Rivoire, K., et al., *The effects of repeated spectroscopic pressure measurements on fluorescence intensity in the cervix*. Am J Obstet Gynecol, 2004. 191(5): p. 1606-17.
29. Lim, L., et al., *Probe pressure effects on human skin diffuse reflectance and fluorescence spectroscopy measurements*. J Biomed Opt, 2011. 16(1): p. 011012.
30. Reif, R., et al., *Analysis of changes in reflectance measurements on biological tissues subjected to different probe pressures*. J Biomed Opt, 2008. 13(1): p. 010502.
31. Ruderman, S., et al., *Analysis of pressure, angle and temporal effects on tissue optical properties from polarization-gated spectroscopic probe measurements*. Biomed Opt Express, 2010. 1(2): p. 489-499.
32. Ti, Y. and W. C. Lin, *Effects of probe contact pressure on in vivo optical spectroscopy*. Opt Express, 2008. 16(6): p. 4250-62.
33. Lin, W. C., et al., *Optical spectroscopy for in-vitro differentiation of pediatric neoplastic and epileptogenic brain lesions*, J Biomed Opt, 2009. 14(1): p. 014028.
34. Chen, P., B. Fernald, and W. Lin, *Estimation of regional hemoglobin concentration in biological tissues using diffuse reflectance spectroscopy with a novel spectral interpretation algorithm*. Physics in Medicine and Biology, 2011. 56(13): p. 3985-4000.
35. Chen, P. C. and W. C. Lin, *Spectral-profile-based algorithm for hemoglobin oxygen saturation determination from diffuse reflectance spectra*. Biomed Opt Express, 2011. 2(5): p. 1082-96.
36. Farrell, T. J., M. S. Patterson, and B. Wilson, *A diffusion theory model of spatially resolved, steady-state diffuse reflectance for the noninvasive determination of tissue optical properties in vivo*. Med Phys, 1992. 19(4): p. 879-88.
37. Pennings, F. A., C. Ince, and G. J. Bouma, *Continuous real-time visualization of the human cerebral microcirculation during arteriovenous malformation surgery using orthogonal polarization spectral imaging*. Neurosurgery, 2006. 59(1): p. 167-71; discussion 167-71.
38. Uhl, E., et al., *Intraoperative detection of early microvasospasm in patients with subarachnoid hemorrhage by* using orthogonal polarization spectral imaging. Neurosurgery, 2003. 52(6): p. 1307-15; discussion 1315-7.
39. Jain, R. K., et al., *Angiogenesis in brain tumours*. Nat Rev Neurosci, 2007. 8(8): p. 610-22.
40. Vajkoczy, P. and M. D. Menger, *Vascular microenvironment in gliomas*. J Neurooncol, 2000. 50(1-2): p. 99-108.
41. Groner, W., et al., *Orthogonal polarization spectral imaging: a new method for study of the microcirculation*. Nat Med, 1999. 5(10): p. 1209-12.
42. Cerny, V., Z. Turek, and R. Parizkova, *Orthogonal polarization spectral imaging*. Physiol Res, 2007. 56(2): p. 141-7.
43. Torp, H., K. Kristoffersen, and B. A. J. Angelsen, *Autocorrelation Techniques in Color-Flow Imaging—Signal Model and Statistical Properties of the Autocorrelation Estimates*. Ieee Transactions on Ultrasonics Ferroelectrics and Frequency Control, 1994. 41(5): p. 604-612.
44. Slaaf, D. W., et al., *A Versatile Incident Illuminator for Intravital Microscopy*. International Journal of Microcirculation-Clinical and Experimental, 1987. 6(4): p. 391-397.

What is claimed is:
1. A system for identifying a site in a tissue of a patient as neoplastic or normal, the system comprising:
   a) a source of electromagnetic signals;
   b) a probe operably connected to the source of electromagnetic signals, for delivering the electromagnetic signals to a plurality of known normal reference tissue sites and a suspected neoplastic tissue site of the patient;
   c) a spectrometer that acquires diffuse reflectance electromagnetic signals returned from the tissue sites and produces a diffuse reflectance spectra from the returned diffuse reflectance electromagnetic signals; and
   d) a system controller operably connected to the spectrometer, wherein the system controller:
      i) analyzes the diffuse reflectance spectra for the suspected neoplastic tissue site of the patient to calculate the following parameters:
         a) absolute hemoglobin concentration, normalized to mean hemoglobin concentration normal measurements to obtain n[Hb],
         b) absolute hemoglobin oxygenation, normalized to mean hemoglobin oxygenation normal measurements to obtain nSatO,
         c) absolute diffuse reflectance intensity of signals having wavelength of about 700 nm, normalized to mean normal Rd(700) measurements to obtain nRd(700),
         d) relative ratio of absorption coefficient $\mu_a$ and reduced scattering coefficient $\mu_s$ between 450 nm and 650 nm, normalized to mean normal $\mu_a(\lambda)/\mu_s(\lambda)$ measurements to obtain $n\mu_a(\lambda)/\mu_s(\lambda)$,
      ii) analyzes the diffuse reflectance spectra from the plurality of known normal reference tissue sites to calculate the following respective standard deviations for each of the parameters:
         a) absolute hemoglobin concentration, normalized to an average hemoglobin concentration from known normal reference tissue measurements to obtain $n[Hb]_{N\_std}$,
         b) absolute hemoglobin oxygenation, normalized to an average hemoglobin oxygenation from known normal reference tissue measurements to obtain $nSatO_{2N\_std}$,
         c) absolute diffuse reflectance intensity of signals having wavelength of about 700 nm, normalized to an average normal Rd(700) from known normal reference tissue measurements to obtain $nRd(700)_{N\_std}$,
         d) relative ratio of absorption coefficient $\mu_a$ and reduced scattering coefficient $\mu_s$ between 450 nm and 650 nm, normalized to an average normal $\mu_a(\lambda)/\mu_s(\lambda)$ from known normal reference tissue measurements to obtain $n\mu_a(\lambda)/\mu_s(\lambda)/\mu_s(\lambda)_{N\_std}$, and
      iii) analyzes n[Hb], $nSatO_2$, nRd(700), and/or $n\mu_a(\lambda)/\mu_s(\lambda)$ calculated from the patient suspected neoplastic tissue site with respect to the standard deviations of those same parameters calculated from the plurality of known normal reference tissue sites of the same patient,
   wherein the suspected neoplastic tissue site is identified by the system controller if:
   $n\mu_a(\lambda)/\mu_s(\lambda)>1+x\times n\mu_a(\lambda)/\mu_s(\lambda)_{N\_std}$ or $n\mu_a(\lambda)/\mu_s(\lambda)<1-x\times\mu n_a(\lambda)/\mu_s(\lambda)_{N\_std}$,
   wherein x is an adjustable cutoff for $n\mu_a(\lambda)/\mu_s(\lambda)$.
2. The system of claim 1, wherein the electromagnetic signals have wavelengths between about 500 nm to about 900 nm, about 600 nm to about 850 nm, or about 650 nm to about 800 nm.
3. The system of claim 1, wherein the spectrometer acquires the diffuse reflectance electromagnetic signals returned from the site at a rate of about 5 Hz or higher.
4. The system of claim 1, wherein the spectrometer acquires the diffuse reflectance electromagnetic signals returned from the site at a rate of about 5 Hz to about 60 Hz.
5. The system of claim 1, wherein the spectrometer acquires the diffuse reflectance electromagnetic signals returned from the site at a rate of about 33 Hz.
6. The system of claim 1, wherein the spectrometer acquires the diffuse reflectance electromagnetic signals returned from the site at a rate of about 60 Hz or higher.
7. The system of claim 1, wherein the adjustable cutoff value is between about 0.5 and about 4.0.
8. The system of claim 1, wherein the adjustable cutoff value is about 2.
9. The system of claim 1, wherein the adjustable cutoff value is about 1.
10. The system of claim 1, wherein the adjustable cutoff value is about 2.
11. The system of claim 1, wherein the adjustable cutoff value is about 1.
12. A system for identifying a site in a tissue of a patient as neoplastic or normal, the system comprising:
   a) a source of electromagnetic signals;
   b) a probe operably connected to the source of electromagnetic signals, for delivering the electromagnetic signals to a plurality of known normal reference tissue sites and a suspected neoplastic tissue site of the patient;
   c) a spectrometer that acquires diffuse reflectance electromagnetic signals returned from the tissue sites and produces a diffuse reflectance spectra from the returned diffuse reflectance electromagnetic signals; and
   d) a system controller operably connected to the spectrometer, wherein the system controller:
      i) analyzes the diffuse reflectance spectra for the suspected neoplastic tissue site of the patient to calculate the following parameters:
         a) absolute hemoglobin concentration, normalized to mean hemoglobin concentration normal measurements to obtain n[Hb], b) absolute hemoglobin oxygenation, normalized to mean hemoglobin oxygenation normal measurements to obtain $nSatO_2$,
c) absolute diffuse reflectance intensity of signals having wavelength of about 700 nm, normalized to mean normal Rd(700) measurements to obtain nRd(700),
d) relative ratio of absorption coefficient $\mu_a$ and reduced scattering coefficient $\mu_s$ between 450 nm and 650 nm, normalized to mean normal $\mu_a(\lambda)/\mu_s(\lambda)$ measurements to obtain $n\mu_a(\kappa)/\mu_s(\lambda)$,
ii) analyzes the diffuse reflectance spectra from the plurality of known normal reference tissue sites to calculate the following respective standard deviations for each of the parameters:
a) absolute hemoglobin concentration, normalized to an average hemoglobin concentration from known normal reference tissue measurements to obtain $n[Hb]_{N\_std}$,
b) absolute hemoglobin oxygenation, normalized to an average hemoglobin oxygenation from known normal reference tissue measurements to obtain $nSatO_{2N\_std}$,
c) absolute diffuse reflectance intensity of signals having wavelength of about 700 nm, normalized to an average normal Rd(700) from known normal reference tissue measurements to obtain $nRd(700)_{N\_std}$,
d) relative ratio of absorption coefficient $\mu_a$ and reduced scattering coefficient $\mu_s$ between 450 nm and 650 nm, normalized to an average normal $\mu_a(\lambda)/\mu_s(\lambda)$ from known normal reference tissue measurements to obtain $n\mu_a(\lambda)/\lambda_s(\lambda)_{N\_std}$, and
iii) analyzes n[Hb], $nSatO_2$, nRd(700), and/or $n\mu_a(\lambda)/\mu_s(\lambda)$ calculated from the patient suspected neoplastic tissue site with respect to the standard deviations of those same parameters calculated from the plurality of known normal reference tissue sites of the same patient, wherein the suspected neoplastic tissue site is identified by the system controller if:

$nSatO_2 > 1 + y \times nSatO_{2N\_std}$ or $nSatO_2 < 1 - y \times nSatO_{2N\_std}$, wherein y is an adjustable cutoff for $nSatO_2$.

13. A system for identifying a site in a tissue of a patient as neoplastic or normal, the system comprising:
a) a source of electromagnetic signals;
b) a probe operably connected to the source of electromagnetic signals, for delivering the electromagnetic signals to a plurality of known normal reference tissue sites and a suspected neoplastic tissue site of the patient;
c) a spectrometer that acquires diffuse reflectance electromagnetic signals returned from the tissue sites and produces a diffuse reflectance spectra from the returned diffuse reflectance electromagnetic signals; and
d) a system controller operably connected to the spectrometer, wherein the system controller:
i) analyzes the diffuse reflectance spectra for the suspected neoplastic tissue site of the patient to calculate the following parameters:
a) absolute hemoglobin concentration, normalized to mean hemoglobin concentration normal measurements to obtain n[Hb],
b) absolute hemoglobin oxygenation, normalized to mean hemoglobin oxygenation normal measurements to obtain $nSatO_2$,
c) absolute diffuse reflectance intensity of signals having wavelength of about 700 nm, normalized to mean normal Rd(700) measurements to obtain nRd(700),
d) relative ratio of absorption coefficient $\mu_a$ and reduced scattering coefficient $\mu_s$ between 450 nm and 650 nm, normalized to mean normal $\mu_a(\lambda)/\mu_s(\lambda)$ measurements to obtain $n\mu_a(\lambda)/\mu_s(\lambda)$,
ii) analyzes the diffuse reflectance spectra from the plurality of known normal reference tissue sites to calculate the following respective standard deviations for each of the parameters:
a) absolute hemoglobin concentration, normalized to an average hemoglobin concentration from known normal reference tissue measurements to obtain $n[Hb]_{N\_std}$,
b) absolute hemoglobin oxygenation, normalized to an average hemoglobin oxygenation from known normal reference tissue measurements to obtain $nSatO_{2N\_std}$,
c) absolute diffuse reflectance intensity of signals having wavelength of about 700 nm, normalized to an average normal Rd(700) from known normal reference tissue measurements to obtain $nRd(700)_{N\_std}$,
d) relative ratio of absorption coefficient $\mu_a$ and reduced scattering coefficient $\mu_s$ between 450 nm and 650 nm, normalized to an average normal $n\mu_a(\lambda)/\mu_s(\lambda)$ from known normal reference tissue measurements to obtain $n\mu_a(\lambda)/\lambda_s(\lambda)_{N\_std}$, and
iii) analyzes n[Hb], $nSatO_2$, nRd(700), and/or $n\mu_a(\lambda)/\mu_s(\lambda)$ calculated from the patient suspected neoplastic tissue site with respect to the standard deviations of those same parameters calculated from the plurality of known normal reference tissue-site-sites of the same patient, wherein the suspected neoplastic tissue site is identified by the system controller if:

$nRd(700) > 1 + z \times nRd(700)_{N\_std}$ or $nRd(700) < 1 - z \times nRd(700)_{N\_std}$ wherein z is an adjustable cutoff for nRd(700).

14. A system for identifying a site in a tissue of a patient as neoplastic or normal, the system comprising:
a) a source of electromagnetic signals;
b) a probe operably connected to the source of electromagnetic signals, for delivering the electromagnetic signals to a plurality of known normal reference tissue sites and a suspected neoplastic tissue site of the patient;
c) a spectrometer that acquires diffuse reflectance electromagnetic signals returned from the tissue sites and produces a diffuse reflectance spectra from the returned diffuse reflectance electromagnetic signals; and
d) a system controller operably connected to the spectrometer, wherein the system controller:
i) analyzes the diffuse reflectance spectra for the suspected neoplastic tissue site of the patient to calculate one or more of the following parameters:
a) absolute hemoglobin concentration, normalized to mean hemoglobin concentration normal measurements to obtain n[Hb],
b) absolute hemoglobin oxygenation, normalized to mean hemoglobin oxygenation normal measurements to obtain $nSatO_2$, c) absolute diffuse reflectance intensity of signals having wavelength of about 700 nm, normalized to mean normal Rd(700) measurements to obtain nRd(700), d) relative ratio of absorption coefficient $\mu_a$ and reduced scattering coefficient $\mu_s$ between 450 nm and 650 nm, normalized to mean normal $\mu_a(\lambda)/\mu_s(\lambda)$ measurements to obtain $n\mu_a(\lambda)/\mu_s(\lambda)$, ii) analyzes the diffuse reflectance spectra from the plurality of known normal reference tissue sites to calculate the following respective standard deviations for each of the parameters:

a) absolute hemoglobin concentration, normalized to an average hemoglobin concentration from known normal reference tissue measurements to obtain $n[Hb]_{N\_std}$, b) absolute hemoglobin oxygenation, normalized to an average hemoglobin oxygenation from known normal reference tissue measurements to obtain $nSatO_{2N\_std}$, c) absolute diffuse reflectance intensity of signals having wavelength of about 700 nm, normalized to an average normal Rd(700) from known normal reference tissue measurements to obtain $nRd(700)_{N\_std}$, d) relative ratio of absorption coefficient $\mu_a$ and reduced scattering coefficient $\mu_s$ between 450 nm and 650 nm, normalized to an average normal $\mu_a(\lambda)/\mu_s(\lambda)$ from known normal reference tissue measurements to obtain $n\mu_a(\lambda)/\mu_s(\lambda)_{N\_std}$, and iii) analyzes n[Hb], $nSatO_2$, nRd(700), and/or $n\mu_a(\lambda)/\mu_s(\lambda)$ calculated from the patient suspected neoplastic tissue site with respect to the standard deviations of those same parameters calculated from the plurality of known normal reference tissue sites of the same patient, wherein the suspected neoplastic tissue site is identified by the system controller if:

a) any one of $nSatO_2$, nRd(700), and $n\mu_a(\lambda)/\mu_s(\lambda)$ is $>1+u\times nSatO_{2N\_std}$, $nRd(700)_{N\_std}$, and $n\mu_a(\lambda)/\mu_s(\lambda)_{N\_std}$, respectively, or b) any one of $nSatO_2$, and nRd(700), and $n\mu_a(\lambda)/\mu_s(\lambda)$ is $<1-u\times nSatO_{2N\_std}$, $nRd(700)_{N\_std}$, and $n\mu_a(\lambda)/\mu_s(\mu)_{N\_std}$, respectively, wherein u is an adjustable cutoff value for $nSatO_2$, nRd(700), and $n\mu_a(\lambda)/\mu_s(\lambda)$.

15. A system for identifying a site in a tissue of a patient as neoplastic or normal, the system comprising:

a) a source of electromagnetic signals;

b) a probe operably connected to the source of electromagnetic signals, for delivering the electromagnetic signals to a plurality of known normal reference tissue sites and a suspected neoplastic tissue site of the patient;

c) a spectrometer that acquires diffuse reflectance electromagnetic signals returned from the tissue sites and produces a diffuse reflectance spectra from the returned diffuse reflectance electromagnetic signals; and d) a system controller operably connected to the spectrometer, wherein the system controller:

i) analyzes the diffuse reflectance spectra for the suspected neoplastic tissue site of the patient to calculate the following parameters:

a) absolute hemoglobin concentration, normalized to mean hemoglobin concentration normal measurements to obtain n[Hb], b) absolute hemoglobin oxygenation, normalized to mean hemoglobin oxygenation normal measurements to obtain $nSatO_2$, c) absolute diffuse reflectance intensity of signals having wavelength of about 700 nm, normalized to mean normal Rd(700) measurements to obtain nRd(700), d) relative ratio of absorption coefficient $\mu_a$ and reduced scattering coefficient $\mu_s$ between 450 nm and 650 nm, normalized to mean normal $\mu_a(\lambda)/\mu_s(\lambda)$ measurements to obtain $n\mu_a(\lambda)/\mu_s(\lambda)$, ii) analyzes the diffuse reflectance spectra from the plurality of known normal reference tissue sites to calculate the following respective standard deviations for each of the parameters:

a) absolute hemoglobin concentration, normalized to an average hemoglobin concentration from known normal reference tissue measurements to obtain $n[Hb]_{N\_std}$, b) absolute hemoglobin oxygenation, normalized to an average hemoglobin oxygenation from known normal reference tissue measurements to obtain $nSatO_{2N\_std}$, c) absolute diffuse reflectance intensity of signals having wavelength of about 700 nm, normalized to an average normal Rd(700) from known normal reference tissue measurements to obtain $nRd(700)_{N\_std}$, d) relative ratio of absorption coefficient $\mu_a$ and reduced scattering coefficient $\mu_s$ between 450 nm and 650 nm, normalized to an average normal $\mu_a(\lambda)/\mu_s(\lambda)$ from known normal reference tissue measurements to obtain $n\mu_a(\lambda)/\mu_s(\lambda)_{N\_std}$, and iii) analyzes n[Hb], $nSatO_2$, nRd(700), and/or $n\mu_a(\lambda)/\mu_s(\lambda)$ calculated from the patient suspected neoplastic tissue site with respect to the standard deviations of those same parameters calculated from the plurality of known normal reference tissue sites of the same patient, wherein the suspected neoplastic tissue site is identified by the system controller if:

a) any two of $nSatO_2$, nRd(700), and $n\mu_a(\lambda)/\mu_s(\lambda)$ is $>1+v\times nSatO_{2N\_std}$, $nRd(700)_{N\_std}$, and $n\mu_a(\lambda)/\mu_s(\lambda)_{N\_std}$, respectively, or b) any two of $nSatO_2$, nRd(700), and $n\mu_a(\lambda)/\mu_s(k)$ is $<1-v\times nSatO_{2N\_std}$, $nRd(700)_{N\_std}$, and $n\mu_a(\lambda)/\mu_s(\lambda)_{N\_std}$, respectively, wherein v is an adjustable cutoff value for $nSatO_2$, nRd(700), and $n\mu_a(\lambda)/\mu_s(\lambda)$.

16. A system for identifying a site in a tissue of a patient as neoplastic or normal, the system comprising:

a) a source of electromagnetic signals;

b) a probe operably connected to the source of electromagnetic signals, for delivering the electromagnetic signals to a plurality of known normal reference tissue sites and a suspected neoplastic tissue site of the patient;

c) a spectrometer that acquires diffuse reflectance electromagnetic signals returned from the tissue sites and produces a diffuse reflectance spectra from the returned diffuse reflectance electromagnetic signals; and d) a system controller operably connected to the spectrometer, wherein the system controller:

i) analyzes the diffuse reflectance spectra for the suspected neoplastic tissue site of the patient to calculate the following parameters:

a) absolute hemoglobin concentration, normalized to mean hemoglobin concentration normal measurements to obtain n[Hb],
b) absolute hemoglobin oxygenation, normalized to mean hemoglobin oxygenation normal measurements to obtain $nSatO_2$),
c) absolute diffuse reflectance intensity of signals having wavelength of about 700 nm, normalized to mean normal Rd(700) measurements to obtain nRd(700),
d) relative ratio of absorption coefficient $\mu_a$ and reduced scattering coefficient $\mu_s$ between 450 nm and 650 nm, normalized to mean normal $\mu_a(\lambda)/\mu_s(\lambda)$ measurements to obtain $n\mu_a(\lambda)/\mu_s(\lambda)$, ii) analyzes the diffuse reflectance spectra from the plurality of known normal reference tissue sites of the patient to calculate the following respective standard deviations for each of the parameters:
a) absolute hemoglobin concentration, normalized to an average hemoglobin concentration from known normal reference tissue measurements to obtain $n[Hb]_{N\_std}$,
b) absolute hemoglobin oxygenation, normalized to an average hemoglobin oxygenation from known normal reference tissue measurements to obtain $nSatO_{2N\_std}$,
c) absolute diffuse reflectance intensity of signals having wavelength of about 700 nm, normalized to an average natural Rd(700) from known normal reference tissue measurements to obtain $nRd(700)_{N\_std}$,
d) relative ratio of absorption coefficient $\mu_a$ and reduced scattering coefficient $\mu_s$ between 450 nm and 650 nm, normalized to an average normal $\mu_a(\lambda)/\mu_s(\lambda)$ from known normal reference tissue measurements to obtain $n\mu_a(\lambda)/\mu_s(\kappa)_{N\_std}$, and iii) analyzes n[Hb], $nSatO_2$, nRd(700), and/or $n\mu_a(\lambda)/\mu_s(\lambda)$ calculated from the patient suspected neoplastic tissue site with respect to the standard deviations of those same parameters calculated from the plurality of known normal reference tissue sites of the same patient, wherein the suspected neoplastic tissue site is identified by the system controller if:
a) all of $nSatO_2$, nRd(700), and $n\mu_a(\lambda)/\mu_s(\lambda)$ are $>1+w\times nSatO_{2N\_std}$, $nRd(700)_{N\_std}$, and $n\mu_a(\lambda)/\mu_s(\lambda)_{N\_std}$, respectively, or
b) all of $nSatO_2$, nRd(700), and $n\mu_a(\lambda)/\mu_s(\lambda)$ are $<1-w\times nSatO_{2N\_std}$, $nRd(700)_{N\_std}$, and $n\mu_a(\lambda)/\mu_s(\lambda)_{N\_std}$, respectively, wherein w is an adjustable cutoff value for $nSatO_2$, nRd(700), and $n\mu_a(\lambda)/\mu_s(\lambda)$.

17. The system of claim 16, wherein the electromagnetic signals have wavelengths between about 500 nm to about 900 nm, about 600 nm to about 850 nm, or about 650 nm to about 800 nm.

18. The system of claim 16, wherein the spectrometer acquires the diffuse reflectance electromagnetic signals returned from the site at a rate of about 5 Hz or higher.

19. The system of claim 16, wherein the spectrometer acquires the diffuse reflectance electromagnetic signals returned from the site at a rate of about 5 Hz to about 60 Hz.

20. The system of claim 16, wherein the spectrometer acquires the diffuse reflectance electromagnetic signals returned from the site at a rate of about 33 Hz.

21. The system of claim 16, wherein the spectrometer acquires the diffuse reflectance electromagnetic signals returned from the site at a rate of about 60 Hz or higher.

22. The system of claim 16, wherein the adjustable cutoff value is between about 0.5 and about 4.0.

* * * * *